United States Patent
An

(10) Patent No.: US 12,412,202 B2
(45) Date of Patent: Sep. 9, 2025

(54) APPARATUS AND METHOD FOR PROVIDING CUSTOMIZED SERVICE

(71) Applicant: LILLYCOVER, INC., Daegu (KR)

(72) Inventor: Sun Hee An, Gyeongsan-si (KR)

(73) Assignee: LILLYCOVER, INC., Daegu (KR)

( * ) Notice: Subject to any disclaimer, the term of this patent is extended or adjusted under 35 U.S.C. 154(b) by 126 days.

(21) Appl. No.: 18/225,684

(22) Filed: Jul. 25, 2023

(65) Prior Publication Data
US 2024/0037622 A1   Feb. 1, 2024

(30) Foreign Application Priority Data

Jul. 27, 2022   (KR) .................. 10-2022-0093259

(51) Int. Cl.
| | |
|---|---|
| *G06Q 30/0601* | (2023.01) |
| *G06Q 10/087* | (2023.01) |
| *G16H 10/20* | (2018.01) |
| *G16H 50/20* | (2018.01) |
| *G06Q 10/083* | (2024.01) |
| *G06Q 10/20* | (2023.01) |

(52) U.S. Cl.
CPC ......... *G06Q 30/0621* (2013.01); *G16H 10/20* (2018.01); *G16H 50/20* (2018.01); *G06Q 10/083* (2013.01); *G06Q 10/087* (2013.01); *G06Q 10/20* (2013.01)

(58) Field of Classification Search
CPC .............. A45D 2044/007; A61K 8/00–99
See application file for complete search history.

(56) References Cited

U.S. PATENT DOCUMENTS

| | | | |
|---|---|---|---|
| 10,902,492 B2 * | 1/2021 | Lu ...................... | G06Q 30/0621 |
| 11,515,043 B1 * | 11/2022 | Choe ................... | A61M 5/3295 |
| 2002/0082745 A1 * | 6/2002 | Wilmott .................. | A61K 8/70 |
| | | | 700/233 |

(Continued)

OTHER PUBLICATIONS

Lillycover. Screen captures from YouTube video clip entitled "Enima, a facility for producing customized cosmetics.". Uploaded on Jan. 12, 2021. <URL: https://www.youtube.com/watch?v=RH95v5N_cml>. (Year: 2021).*

(Continued)

*Primary Examiner* — Bion A Shelden
(74) *Attorney, Agent, or Firm* — PnK IP LLC

(57) ABSTRACT

Provided are an apparatus and method for a customized service. The customized service providing method is a customized service providing method performed by a processor of a customized service providing device, including: collecting survey response information and images from a customer in response to survey request information and image request information provided to a customer for diagnosis of at least one of the skin of the customer and a scalp of the customer; generating a diagnosis result for at least one of the skin of the customer and a scalp of the customer based on the survey response information and images; generating and providing recipe information for manufacturing a customized product with respect to the diagnosis result; and transmitting, to a product manufacturing device, manufacturing instruction signal of customized products including recipe information, based on customized product purchase signals received from the customer.

13 Claims, 19 Drawing Sheets

(56) References Cited

U.S. PATENT DOCUMENTS

| | | | | |
|---|---|---|---|---|
| 2008/0243523 | A1* | 10/2008 | Beilis | G06Q 30/0603 705/1.1 |
| 2015/0088307 | A1* | 3/2015 | Ackerman | G06Q 10/087 700/241 |
| 2017/0228892 | A1* | 8/2017 | Nichol | A45D 44/005 |
| 2017/0262798 | A1* | 9/2017 | Kosseifi | H04W 64/00 |
| 2018/0368558 | A1* | 12/2018 | Park | A45D 44/005 |
| 2019/0137957 | A1* | 5/2019 | Bly | A61K 8/362 |
| 2019/0378187 | A1* | 12/2019 | Lin | G06Q 10/063112 |
| 2020/0113313 | A1* | 4/2020 | Kumpan-Bahrami | A61B 5/4839 |
| 2021/0378389 | A1* | 12/2021 | Hong | A61B 5/445 |
| 2022/0091596 | A1* | 3/2022 | Lee | A45D 44/005 |
| 2022/0129965 | A1* | 4/2022 | Ford | A61K 8/602 |
| 2022/0401014 | A1* | 12/2022 | Han | G16H 40/63 |
| 2023/0178238 | A1* | 6/2023 | Park | G16H 30/40 705/2 |
| 2024/0032856 | A1* | 2/2024 | Park | G16H 50/20 |
| 2024/0203589 | A1* | 6/2024 | Park | G16H 50/20 |

OTHER PUBLICATIONS

Lillycover. Screen captures from YouTube video clip entitled "(EN) Lillycover". Uploaded on Nov. 16, 2020. <URL: https://www.youtube.com/watch?v=AwwSV1eQ1H8>. (Year: 2020).*

Lillycover. Screen captures from YouTube video clip entitled "CES2020 x Lillycover". Uploaded on Jan. 2, 2020. <URL: https://www.youtube.com/watch?v=MFYpVZhamcA>. (Year: 2020).*

Lillycover. Screen captures from YouTube video clip entitled "Lillycover: Balanx Pop Up". Uploaded on Apr. 28, 2021. <URL: https://www.youtube.com/watch?v=MfSi8eb1eW0>. (Year: 2021).*

Lillycover. Screen captures from YouTube video clip entitled "Lillycover Application [Skin Diagnosis]". Uploaded on Jun. 29, 2018. <URL: https://www.youtube.com/watch?v=Vrj7E1zPIDI>. (Year: 2018).*

* cited by examiner

FIG. 4

| | | Dry oil content not more than 35 & dryness not less than 60 | | | | Neutral/complex oil content less than 70 | | | | | | | | Oily oil content not less than 70 | | | | | | | |
|---|---|---|---|---|---|---|---|---|---|---|---|---|---|---|---|---|---|---|---|---|---|
| | | Dry Dry | | | | Dehydration Part more than 45 | | | | Adequate moisture Complexity not more than 70 | | | | Dehydration Imbalance more than 45 | | | | Adequate moisture Oily not more than 45 | | | |
| | | Resistance B not more than 50 | | Sensitivity S more than 50 | | Resistance B not more than 50 | | Sensitivity S more than 50 | | Resistance B not more than 50 | | Sensitivity S more than 50 | | Resistance B not more than 50 | | Sensitivity S Seborrheic T more than 50 | | Resistance B not more than 50 | | Sensitivity S Seborrheic T more than 50 | |
| | | keratin level | redness level | keratin level | redness level | keratin level | redness level | keratin level | redness level | keratin level | redness level | keratin level | redness level | keratin level | redness level | keratin level | redness level | keratin level | redness level | Not more than 50 | More than 50 |
| | | survey | | survey | | survey | | survey | | survey | | survey | | survey | | survey | | survey | | survey | survey |
| Low risk of hair loss Non 45 or less Hair count per pore 40% Hair thickness 40% forehead width ratio 20% | Damaged hair DaMaged more than 50 | DBNM | | DSNM | | PBNM | | PSNM | | CBBN | | CSNM | | IBNM | | ISNM | | OBNM | | OSNM | OTNM |
| | Healthy hair Healthy not more than 50 | DBNH | | DSNH | | PBNH | | PSNH | | CBNH | | CSNH | | IBNH | | ISNH | | OBNH | | OSNH | OTNH |
| High risk of hair loss Alopecia more than 45 Hair count per pore 40% Hair thickness 40% forehead width ratio 20% | Damaged hair DaMaged more than 50 | DBAM | | DSAM | | PBAM | | PSAM | | CBAM | | CSAM | | IBAM | | ISAM | | OBAM | | OSAM | OTAM |
| | Healthy hair Healthy not more than 50 | DBAH | | DSAH | | PBAH | | PSAH | | CBAH | | CSAH | | IBAH | | ISAH | | OBAH | | OSAH | OTAH |

| resistance | sensitivity | seborrhea |
|---|---|---|
| 1~50 | 51~100 | |
| | 51~75 | 76~100 |

D (Dry) – Dry scalp
C (Complexity) – (neutral/complex) adequate moisture
P (Part) – (neutral/complex) dehydration
O (Oily) – (oily) adequate moisture
I (Imbalance) – (oily) dehydration
B (Barrier) – Resistance (keratin level+redness level↓+survey)
S (Sensitive) – Sensitivity (keratinlevel↑+rednesslevel↑+survey)
T (Trouble) – Seborrhea (oily+ keratinlevel↑+rednesslevel↑+survey)
N (non) – Low risk of hair loss (number of hairs per pore 40% + hair thickness 40% + forehead width ratio 20%) + survey
A (alopecia) – Hair loss in progress (number of hairs per pore 40% + hair thickness 40% + forehead width ratio 20%) + survey
M (damaged)– Damaged hair (survey + thin hair)
H (Healthy)– Healthy hair (survey + hair thickness is thick and consistent)

FIG. 5D

▷ Skin care

- replenish enough moisture with a moisture pack.
- be sure to pack brightening functional products.
- be careful not to increase the skin temperature.

▷ muscle direction massage, lifting massage

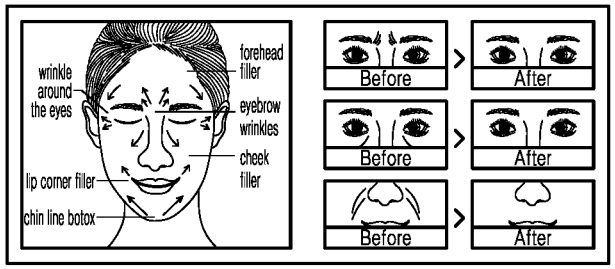

■ Solution (recipe maintenance)

| previous order analysis | | present order analysis | |
|---|---|---|---|
| skin type | PBTV | skin type | PBTV |
| recommended Base | lotion heavy essence heavy | recommended Base | lotion heavy essence heavy |
| intensive care | moisturizing \| brightening | 집중 관리 | brightening \| moisturizing |
| flushing care Careful pigmentation Need improvement | | pigmentation Need improvement need rehydration | |

▷ current order analysis

The pore size is relatively small.
keep an eye on it to make sure it stays on track.
you seems to have no sensitivity.
keep an eye on it to make sure it stays on track.

FIG. 6D

▷ Scalp care

- Remove keratin from the scalp with a keratin remover.
- Protect your hair with a treatment.
- Be careful not to lose your hair.

▷ Scalp massage

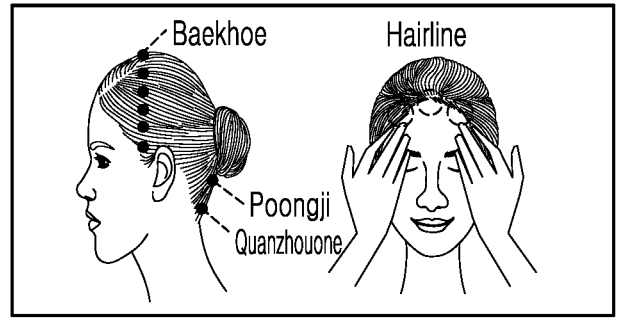

■ Solution (recipe maintenance)

| previous order analysis | | present order analysis | |
|---|---|---|---|
| scalp type | PBNH | scalp type | PBNH |
| Recommended Base | shampoo Light treatment heavy tonic light | Recommended Base | shampoo Light treatment heavy tonic light |
| Intensive care | treatment | Intensive care | treatment |
| Keratin care Careful Damaged hair Need improvement | | Damaged hair Need improvement Protein Need supplement | |

▷ present order analysis

Your scalp lacks moisture. Please increase your water intake. You seem to have many keratin. Remove keratin with a keratin remover...

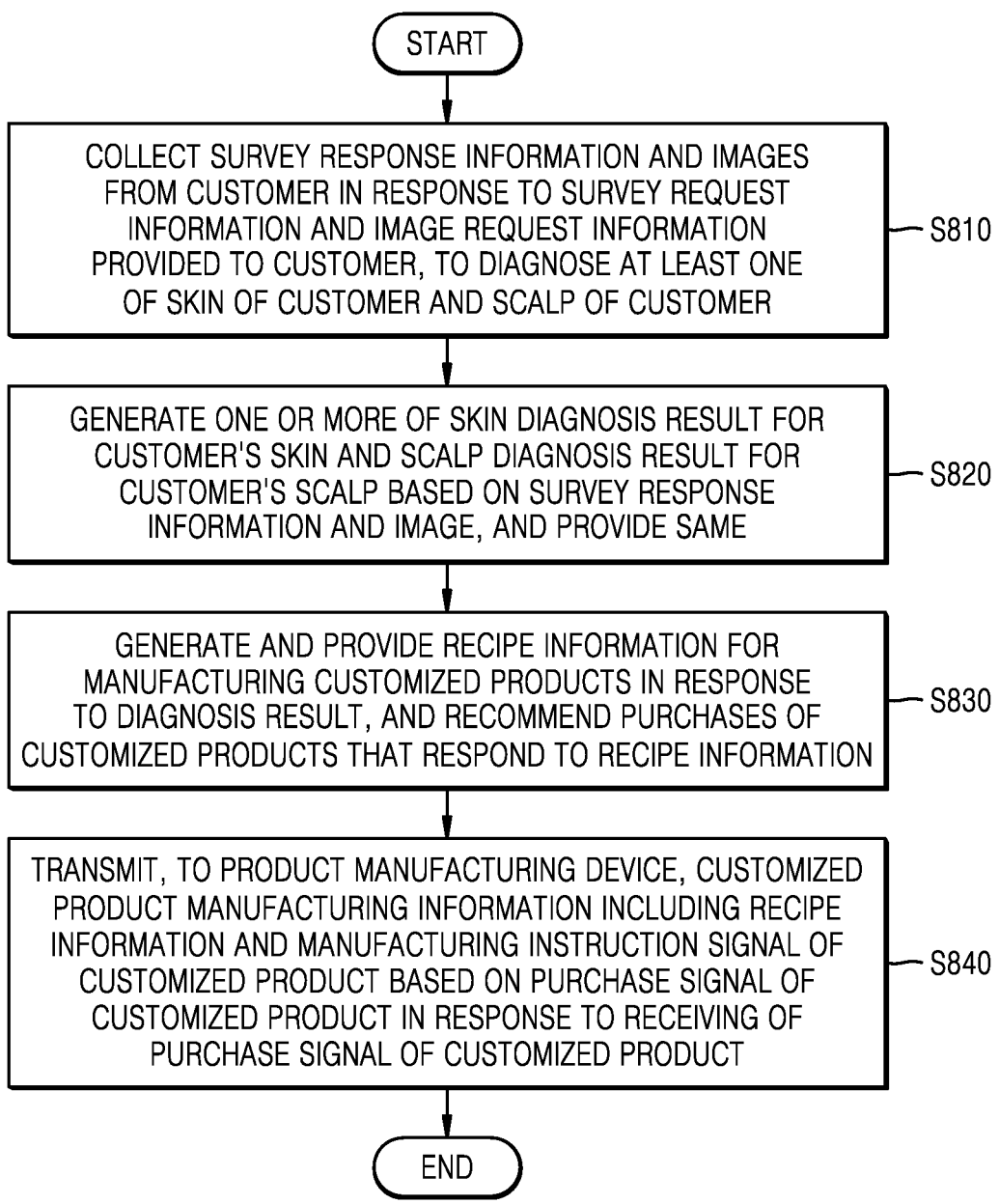

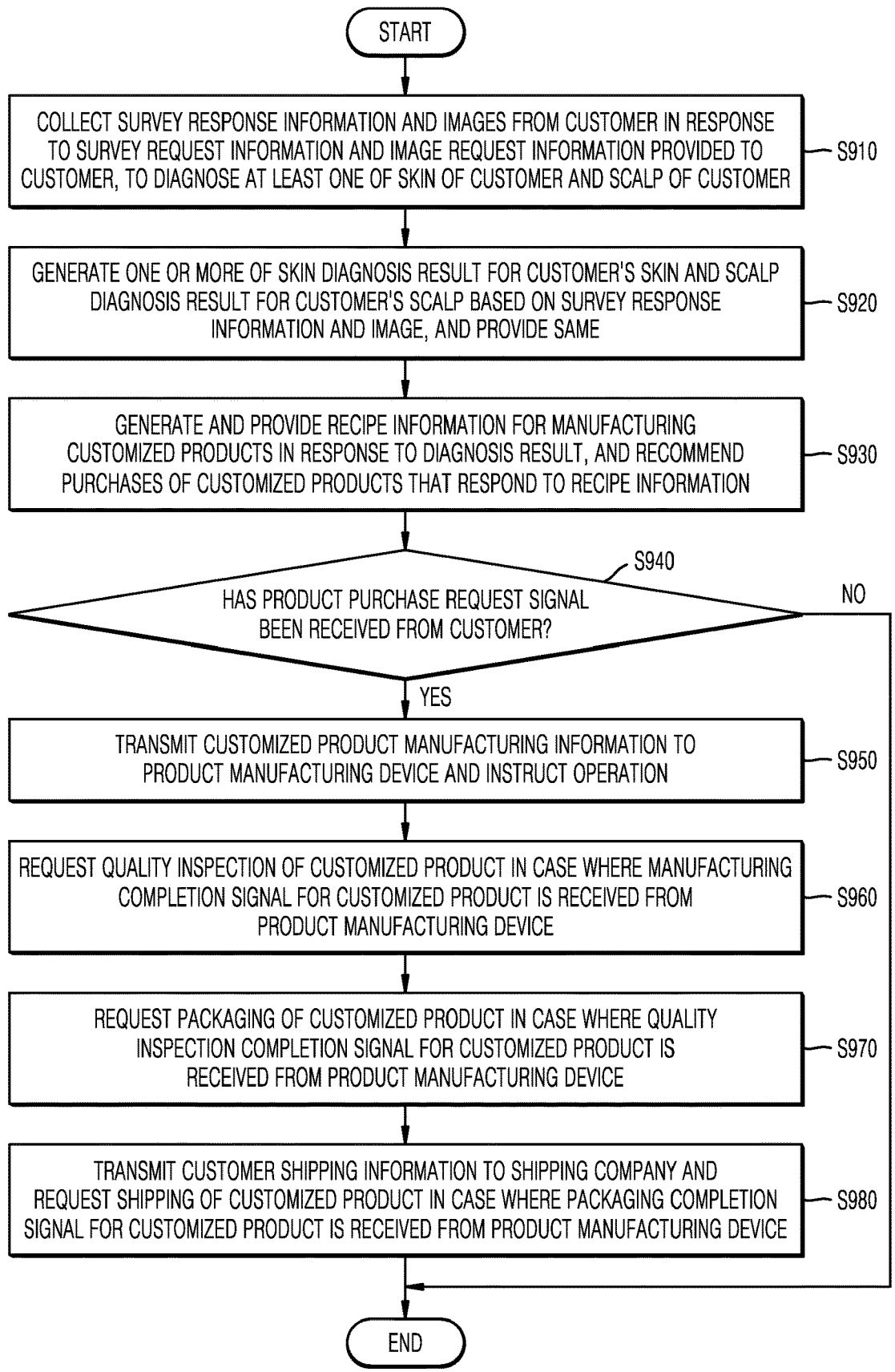

APPARATUS AND METHOD FOR PROVIDING CUSTOMIZED SERVICE

CROSS-REFERENCE TO RELATED APPLICATION

This application claims priority from and the benefit of Korean Patent Application No. 10-2022-0093259, filed on Jul. 27, 2022, which is hereby incorporated by reference for all purposes as if fully set forth herein.

BACKGROUND

Field

Embodiments of the invention relate generally to an apparatus and method for a customized service, by which a diagnosis result for at least one of a skin of the customer and a scalp of the customer is generated and based on the diagnostic results, a customized product is manufactured.

Discussion of the Background

The skin, which covers the surface of the human body, consists of three layers of composite tissue, including the epidermis, dermis, and subcutaneous fat, to protect the body's internal tissues from the external environment and maintain antibiotic properties, and is a very important part of the body that performs various organ functions such as temperature regulation, secretion, and sensory functions. In recent years, with the improvement of living standards and the desire to pursue a beautiful and healthy life in consideration of quality of life, the condition of skin care has emerged as a very important factor in judging one's appearance, and the interest in skin care has increased in order to maintain young, firm, and healthy skin, commonly referred to as youthful skin, resulting in a significant investment of money and time in skin care.

Therefore, women are interested in skin care, but recently men have also increased their interest in appearance. In particular, scalp and skin care are also of great interest as symptoms comparable to serious diseases in modern people such as alopecia are caused by fine dust and stress.

The above information disclosed in this Background section is only for understanding of the background of the inventive concepts, and, therefore, it may contain information that does not constitute prior art.

SUMMARY

Apparatus and method for providing customized service constructed according to illustrative implementations of the invention are capable of generating a diagnosis result for a customer's skin and/or scalp from a customer's image and survey response results, and to manufacture and provide a customized skin and/or scalp product based on the recipe information generated according to the diagnosis result.

Embodiments of the invention are also capable of determining and providing the diagnosis result for the customer's scalp as one of a plurality of scalp types classified in the form of myers-briggs-type indicator (MBTI).

Embodiments of the invention are also capable of receiving, from the customer, a purchase request for a skin product and/or scalp product based on the recipe information generated according to the diagnosis result so as to manufacture a customized skin product and/or scalp product by a product manufacturing device.

Embodiments of the invention are also capable of providing for shipping to a customer's address as a customized skin product and/or scalp product is completed.

Embodiments of the invention are not limited to the objectives described above, and other objectives and advantages of the present disclosure not described can be understood from the following description, and will be more clearly understood from the embodiments of the present disclosure. It will also be appreciated that the objectives and advantages of the present disclosure can be realized by the means described in the patent claims and combinations thereof.

Additional features of the inventive concepts will be set forth in the description which follows, and in part will be apparent from the description, or may be learned by practice of the inventive concepts.

According to one aspect of the invention, a method for providing customized service performed by a processor of a customized service providing device, the method includes the steps of: collecting survey response information and images from a customer in response to survey request information and image request information provided to a customer for diagnosis of at least one of the skin of the customer and a scalp of the customer; generating a diagnosis result for at least one of the skin of the customer and a scalp of the customer based on the survey response information and images; generating and providing recipe information for manufacturing a customized product with respect to the diagnosis result; and transmitting, to a product manufacturing device, manufacturing instruction signal of customized product including recipe information, based on customized product purchase signals received from the customer.

The step of generating the diagnosis result may includes a step of generating, based on survey response information and images, a scalp diagnosis result for scalp items for the customer's scalp including oil and moisture, sensitivity, hair thickness, hair damage, hair loss, and keratin.

The step of generating the diagnosis result may further include a step of determining the scalp diagnosis result for the customer as one of a plurality of scalp types classified in MBTI form.

The plurality of scalp types classified in the form of MBTI may include 48 scalp types based on 12 scales: dry scalp (D: dry), adequate moisture for neutral scalp and complex scalp (C: complexity), lack of moisture for neutral scalp and complex scalp (P: part), adequate moisture for oily scalp (O: oily), lack of moisture for oily scalp (I: imbalance), resistant scalp (B: barrier), sensitive scalp (S: sensitive), seborrheic scalp (T: trouble), low hair loss concern (N: non), hair loss in progress (A: alopecia), damaged hair (M: damaged), and healthy hair (H: healthy).

The method may further include a step of providing a contactless coaching service to the customer after the step of generating the diagnosis result, wherein the step of providing the contactless coaching service includes the steps of: matching experts for each customer; obtaining a diagnosis result for the at least one of a skin of the customer and a scalp of the customer generated by a matched expert and coaching data based on recipe information corresponding to the diagnosis result for the at least one of a skin of the customer and a scalp of the customer and manufactured customized product information; and providing the coaching data to the customer at a preset time and/or a preset period.

The method may further include steps of: after the step of transmitting the manufacturing instruction signal of the customized products to the product manufacturing device, requesting quality inspection of the customized product in the case where a manufacturing completion signal for the customized product is received from the product manufacturing device; requesting packaging of the customized product in the case where a quality inspection completion signal for the customized product is received from the product manufacturing device; and transmitting customer shipping information to a shipping company in the case where a packaging completion signal for the customized product is received from the product manufacturing device and requesting shipping of the customized product.

The method may further include steps of: before the transmitting a manufacturing instruction signal of a customized product, transmitting maintenance request information including raw material inventory request information, container inventory request information, status request information, and manufacturing environment request information to each of a plurality of product manufacturing devices; receiving, from each of the plurality of product manufacturing devices, maintenance response information including raw material inventory response information, container inventory response information, status response information, and manufacturing environment response information, in response to the maintenance request information; and selecting at least one product manufacturing device capable of manufacturing the customized product based on the maintenance response information.

According to another aspect of the invention, a computer-readable recording media having thereon a computer program for executing a method for providing customized service performed by a processor of a customized service providing device, wherein the method includes the steps of: collecting survey response information and images from a customer in response to survey request information and image request information provided to a customer for diagnosis of at least one of the skin of the customer and a scalp of the customer; generating a diagnosis result for at least one of the skin of the customer and a scalp of the customer based on the survey response information and images; generating and providing recipe information for manufacturing a customized product with respect to the diagnosis result; and transmitting, to a product manufacturing device, manufacturing instruction signal of customized product including recipe information, based on customized product purchase signals received from the customer.

According to still another aspect of the invention, a customized service providing device includes: a processor; and a memory operatively connected to the processor and storing at least one code executed by the processor, wherein the memory stores a code that causes, when executed through the processor, the processor to: collect survey response information and images from a customer in response to survey request information and image request information which have been provided to the customer for diagnosis of at least one of a skin of the customer and a scalp of the customer; generate a diagnosis result for the at least one of a skin of the customer and a scalp of the customer based on the survey response information and images; generate and provide recipe information for manufacturing a customized product corresponding to the diagnosis result; and transmit a manufacturing instruction signal of a customized product including the recipe information to a product manufacturing device based on a customized product purchase signal received from the customer.

It is to be understood that both the foregoing general description and the following detailed description are illustrative and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate illustrative embodiments of the invention, and together with the description serve to explain the inventive concepts.

FIG. 4 shows an example diagram of a scalp diagnosis criteria table expressed in MBTI form to generate a customer's scalp diagnosis result according to an embodiment;

FIG. 5A to 5F shows an example view of a skin diagnosis result for a customer and a solution according to an embodiment;

FIG. 6A to 6F shows an example view of a scalp diagnosis result for a customer and a solution according to an embodiment;

FIGS. 8 and 9 are flowcharts for explaining a method of providing a customized service according to an embodiment.

DETAILED DESCRIPTION

Figure 1:
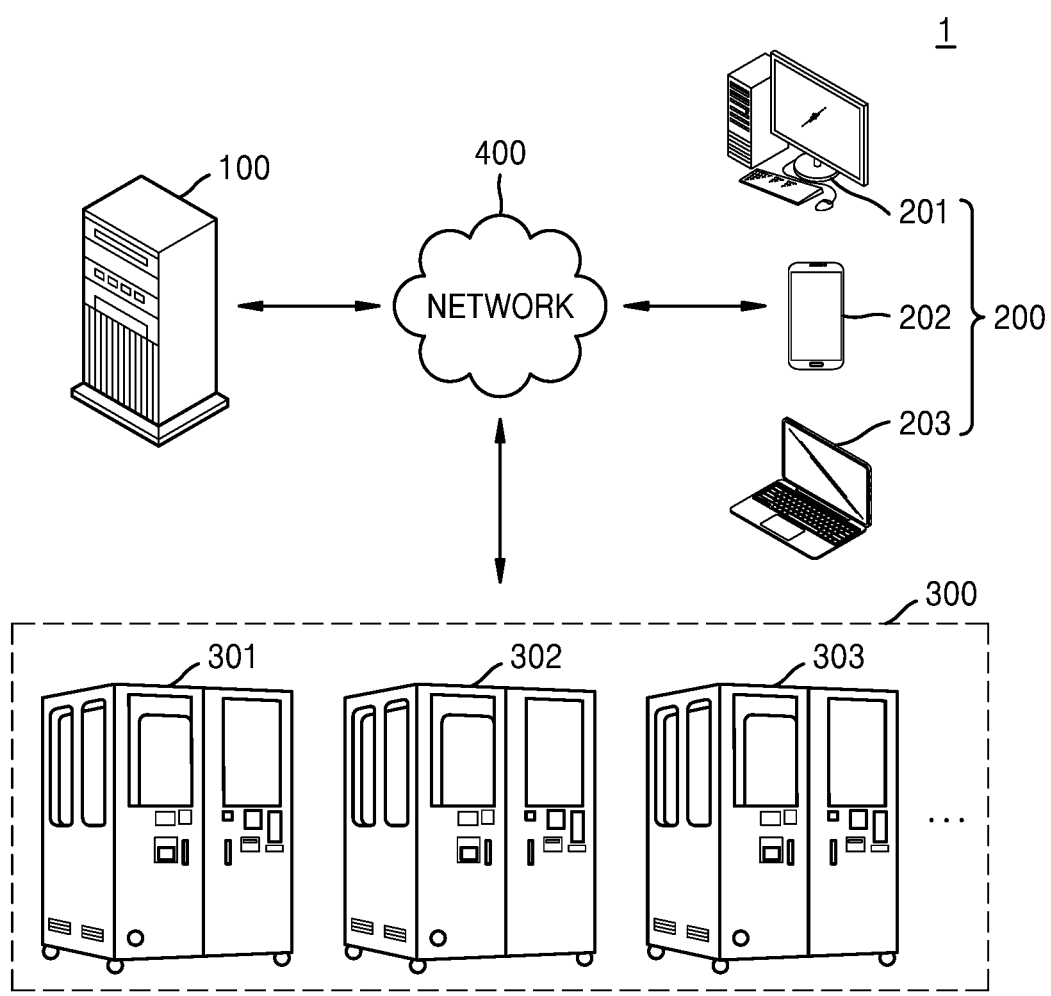
FIG. 1 shows an example diagram illustrating a customized service providing environment according to an embodiment.

In the following description, for the purposes of explanation, numerous specific details are set forth in order to provide a thorough understanding of various embodiments or implementations of the invention. As used herein "embodiments" and "implementations" are interchangeable words that are non-limiting examples of devices or methods employing one or more of the inventive concepts disclosed herein. It is apparent, however, that various embodiments may be practiced without these specific details or with one or more equivalent arrangements. In other instances, well-known structures and devices are shown in block diagram form in order to avoid unnecessarily obscuring various embodiments. Further, various embodiments may be different, but do not have to be exclusive. For example, specific shapes, configurations, and characteristics of an embodiment may be used or implemented in another embodiment without departing from the inventive concepts.

Unless otherwise specified, the illustrated embodiments are to be understood as providing illustrative features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

FIG. 1 shows an example diagram illustrating a customized service providing environment according to an embodiment. Referring to FIG. 1, a customized service providing environment 1 may include a customized service providing device 100 (hereinafter referred to as a service providing device), a customer terminal 200, a product manufacturing device 300, and a network 400.

The service providing device 100 may transmit survey request information and image request information to the customer terminal 200 connected via the network 400, for diagnosis of one or more of the customer's skin and scalp.

The survey request information may include questions to determine one or more of the customer's skin condition and scalp condition, such as, for example, the number of times the customer washes his or her face (for example, twice a day), the degree of skin tightness before and after washing his or her face, the types of skin products currently being used (for example, face wash, foundation, color cosmetics, packs, etc.) and how they feel after use, the number of times the customer washes his or her hair (for example, once a day), the degree of scalp tightness after washing his or her hair, and the types of hair products currently being used (for example, shampoo, conditioner, treatment, etc.) and how they feel after use.

In addition, the image request information is a plurality of requested images capable of determining one or more of the customer's skin condition and scalp condition, and includes front and side images of the customer's face, T zone image in which sebum is concentrated, customer's hairline image, and the customer's scalp image.

In some embodiments, the service providing device 100 may provide, to the customer terminal 200, photographing setting information in response to specification information of the customer terminal 200. This can be provided to obtain optimal images, because a camera included in the customer terminal 200 varies. In this regard, the shooting setting degree may include brightness, sensitivity, contrast, focus, shooting composition guide information, and the like.

The service providing device 100 may collect, from the customer terminal 200, survey response information and images as a response to survey request information and image request information.

The service providing device 100 may generate one or more of a skin diagnosis result for the customer's skin and a scalp diagnosis result for the customer's scalp based on the survey response information and image, and provide the same to the customer terminal 200.

The service providing device 100 may generate, as a skin diagnosis result, a diagnosis result for skin items for the customer's skin including oil and moisture, sensitivity, pigmentation, wrinkles, redness, and pores. In addition, the service providing device 100 may generate, as a scalp diagnosis result, a diagnosis result for scalp items of the customer's scalp including oil and moisture, sensitivity, hair thickness, hair damage, hair loss, and keratin. In some embodiments, the service providing device 100 may determine the scalp diagnosis result as one of a plurality of scalp types classified in MBTI form. Generally, MBTI is a method of psychological assessment for individuals, capable of representing a total of 16 personality types. However, in some embodiments, the term "MBTI" is not used for measuring human psychology; instead, it is employed to express the diagnostic results of scalp in the form of MBTI. In other words, in some embodiments, "MBTI" may be an informal term used to link scalp type indicators to personality type indicators. It is intended to be utilized for connecting scalp type indicators to personality type indicators in an unofficial capacity.

The service providing device 100 may provide the customer terminal 200 with a solution capable of solving problems with one or more of a skin diagnosis result and a scalp diagnosis result. In some embodiments, the solution may include a first solution, a second solution, and a third solution.

The first solution may provide previous and current images and scores for one or more of the skin diagnosis result and scalp diagnosis result, and may include comments to address the issue.

The second solution may provide comments for management of one or more of the skin diagnosis result and the scalp diagnosis result, a skin massage method, and a result comparison image of before/after when the skin massage is performed using the corresponding method. In addition, the second solution may include product recipe information for providing a customized product for one or more of a skin diagnosis result and a scalp diagnosis result.

The third solution may include a contactless coaching service provided to the customer to solve the issue regarding one or more of a skin diagnosis result and a scalp diagnosis result. The contactless coaching service may match experts for each customer, obtain a diagnosis result for one or more of the customer's skin and scalp generated by the matched expert, and coaching data based on recipe information corresponding to the diagnosis result for one or more of the customer's skin and scalp and manufactured customized cosmetics information, and provide the coaching data to the customer at a preset time and/or cycle. In some embodiments, an expert terminal (not shown) connected through the service providing device 100 and the network 400 may be further included to provide a contactless coaching service.

The service providing device 100 may provide, to the customer terminal 200, recipe information of a product corresponding to one or more of a skin diagnosis result and a scalp diagnosis result, and may recommend purchase of a customized product corresponding to the recipe information.

When a purchase signal for a customized product corresponding to recipe information is received from the customer terminal 200, the service providing device 100 transmits customized product manufacturing information to the product manufacturing device 300 and may instruct a customized product manufacturing operation. In this regard, the customized product manufacturing information may include one or more of recipe information corresponding to one or more of a skin diagnosis result and a scalp diagnosis result for the customer, raw material formulation information, container information, and mixing information.

In the case where a manufacturing completion signal for the customized product is received from the product manufacturing device 300, the service providing device 100 may request quality inspection of the customized product. In this regard, the quality inspection of the customized product may be performed in the product manufacturing device 300. Alternatively, the product manufacturing device 300 which has received the request of the service providing device 100, may commission an external quality evaluation company (not shown) to perform a quality inspection.

In the case where a quality inspection completion signal for the customized product is received from the product manufacturing device 300, the service providing device 100 may request packaging for the customized product.

In the case where a packaging completion signal for the customized product is received from the product manufacturing device 300, the service providing device 100 may transmit customer shipping information to a shipping company (not shown) and request shipping of the customized product. The shipping company may pick up the customized product from the warehouse of the product manufacturing device 300 and ship the same to the customer.

In some embodiments, prior to instructing the product manufacturing device 300 to perform an operation, the service providing device 100 may transmit maintenance request information including raw material inventory request information, container inventory request information, status request information, and manufacturing environment request information to each of a plurality of product manufacturing devices 300. The service providing device 100 may receive maintenance response information in response to maintenance request information from each of the plurality of product manufacturing devices 300. The service providing device 100 may select at least one of the product manufacturing devices 300 capable of manufacturing a customized product based on the maintenance response information.

In some embodiments, the service providing device 100 may exist independently in the form of a server, or the functions provided by the service providing device 100 may be implemented in the form of an application and loaded into the customer terminal 200.

The customer terminal 200 may receive a customized service by accessing a customized service providing application and/or a customized service providing site provided by the service providing device 100.

The customer terminal 200 may include a communication terminal capable of performing the function of a computing device (not shown), and may include a desktop computer 201, a smartphone 202, and a laptop computer 203, operated by a user, as well as a tablet PC, a smart TV, a mobile phone, a personal digital assistant (PDA), a media player, a micro server, a global positioning system (GPS) device, an e-book reader, a digital broadcasting terminal, a navigation device, a kiosk, an MP3 player, a digital camera, home appliances, and other mobile or non-mobile computing devices. but is not limited thereto. In addition, the customer terminal 200 may be a wearable terminal having a communication function and data processing function, such as a watch, glasses, hair band, and a ring. The customer terminal 200 is not limited thereto, and a terminal capable of web browsing may be used herein without limitation.

The product manufacturing device (300: 301, 302, 303, . . . ) may manufacture one or more of a customized skin product and a customized scalp product by receiving a product manufacturing instruction signal and customized product manufacturing information from the service providing device 100.

The product manufacturing device 300 may, in response to the maintenance request information received from the service providing device 100, generate maintenance response information including raw material inventory response information, container inventory response information, status response information, and manufacturing environment response information and transmit the same to the service providing device 100. In this regard, the status response information may include whether or not the product manufacturing device 300 is operating normally, the number of production instructions, the number of manufacturing completions, the defect rate, workers, the manufacturing progress phase (for example, container insertion, container separation, raw material discharge, container coupling, stirring, etc.), raw material discharge amount, raw material expiration date, raw material order status, raw material purchase status, etc. In addition, the manufacturing environment response information may include temperature and humidity inside the product manufacturing device 300 and internal cleanliness thereof.

The product manufacturing device 300 may perform quality inspection on a customized product in response to a quality inspection request signal from the service providing device 100, or may commission an external quality evaluation company to perform the quality inspection. The product manufacturing device 300 may transmit a quality inspection result of the customized product to the service providing device 100.

The product manufacturing device 300 may perform packaging for customized products in response to a packaging request signal for customized products.

The network 400 may connect the service providing device 100, the customer terminal 200, and the product manufacturing device 300 to each other. The network 400 may include, for example, wired networks such as a local area network (LAN), a wide area network (WAN), a metropolitan area network (MAN), and an integrated service digital network (ISDN), and a wireless network such as a wireless LAN (WLAN), code-division multiple access (CDMA), and satellite communication, and the scope of the present disclosure is not limited thereto. In addition, the network 400 may transmit and receive information using short-range communication and/or long-range communication. In this regard, the short-range communication may include Bluetooth, radio frequency identification (RFID), infrared data association (IrDA), ultra-wideband (UWB), ZigBee, and Wi-Fi technologies, and the long-range communication may include code-division multiple access (CDMA), frequency-division multiple access (FDMA), time-division multiple access (TDMA), orthogonal frequency-division multiple access (OFDMA), and single carrier frequency-division multiple access (SC-FDMA) technology.

The network 400 may include connections among network elements such as hubs, bridges, routers, and switches. Network 400 may include one or more connected networks, such as multiple network environments, including public networks such as the Internet and private networks such as secure enterprise private networks. Access to network 400 may be provided through one or more wired or wireless access networks.

Furthermore, the network 400 may support controller area network (CAN) communication, vehicle to infrastructure (V2I) communication, vehicle to everything (V2X) communication, wireless access in vehicular environment (WAVE) communication technology, and internet of things (IoT) network and/or 5G communication that exchanges and processes information between distributed components such as objects.

Figure 2:
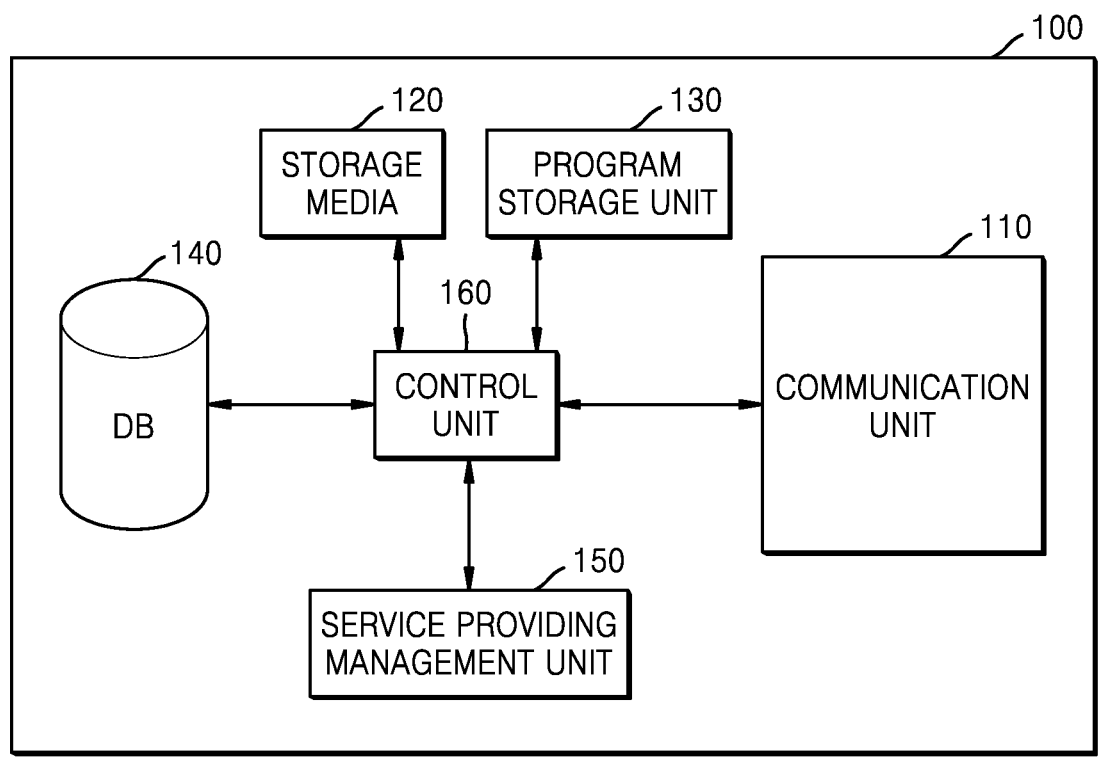
FIG. 2 shows a block diagram schematically illustrating the configuration of a customized service providing device according to an embodiment.

FIG. 2 shows a block diagram schematically illustrating the configuration of a customized service providing device according to an embodiment; In the following description, descriptions that have been provided in connection with FIG. 1 will be omitted. Referring to FIG. 2, a customized service providing device 100 may include a communication unit 110, a storage media 120, a program storage unit 130, a database 140, a service providing management unit 150, and a control unit 160.

The communication unit 110 may provide, in conjunction with the network 400, a communication interface required to provide transmission/reception signals among the service providing device 100, the customer terminal 200, and the product manufacturing device 300 in the form of packet data. Furthermore, the communication unit 110 may transmit a certain information request signal processed by the service providing management unit 150 to the customer terminal 200 and/or the product manufacturing device 300, and may receive a certain information response signal from the customer terminal 200 and/or the product manufacturing device 300. In this regard, the communication network is a media that connects the service providing device 100, the customer terminal 200, and the product manufacturing device 300 to each other, and may include a path providing an access path that allows the customer terminal 200 and/or the product manufacturing device 300 to access the service providing device 100 and to transmit/receive information. In addition, the communication unit 110 may be a device including hardware and software necessary for transmitting and receiving a signal such as a control signal or a data signal to and from another network device through a wired or wireless connection.

The storage media 120 may temporarily or permanently store data processed by the control unit 160. In some embodiments, the storage media 120 may include magnetic storage media or flash storage media, and the scope of present disclosure is not limited thereto. The storage media 120 may include built-in memory and/or external memory, and may include: a volatile memory such as DRAM, SRAM, or SDRAM, a non-volatile memory such as one time programmable ROM (OTPROM), PROM, EPROM, EEPROM, mask ROM, flash ROM, NAND flash memory, or NOR flash memory, a flash drive such as SSD, a compact flash (CF) card, an SD card, a micro-SD card, a mini-SD card, an Xd card, or a memory stick, or a storage device such as an HDD.

The program storage unit 130 includes control software which transmits survey request information and image request information to the customer terminal 200 for diagnosis of one or more of the skin of the customer and a scalp of the customer, collects survey response information and images from the customer terminal 200, generates and provides a diagnosis result for one or more of the skin of the customer and a scalp of the customer based on the survey response information and images, creates and provides a solution that solves an issue regarding one or more of the skin of the customer and a scalp of the customer in response to the diagnosis result, recommends the purchase of a product manufactured according to recipe information included in the solution, transmits maintenance request information to each of the plurality of product manufacturing devices 300 in response to a product purchase request signal, receives maintenance response information in response to the maintenance request information from each of the plurality of product manufacturing devices 300, selects at least one of the product manufacturing devices 300 capable of manufacturing a customized product based on the maintenance response information, transmits customized product manufacturing information to the selected product manufacturing device and instructs product manufacturing, requests quality inspection of the customized product in the case where a manufacturing completion signal for the customized product is received from the product manufacturing unit 300, requests packaging for a customized product from the product manufacturing unit 300, transmits customer shipping information to a shipping company, and requests shipping of the customized product.

The database 140 may include a management database for storing various information for manufacturing customized products. For example, product manufacturing information including recipe information, raw material formulation information, container information, and stirring information, for skin products and scalp products, may be stored in the management database. In addition, maintenance response information received from the product manufacturing device 300 may be stored in the management database. The maintenance response information may include raw material inventory response information, container inventory response information, status response information, and manufacturing environment response information. In addition, the management database may store quality inspection result information for customized products. In addition, the management database may store expert profile information and coaching data generated by the expert for providing a contactless coaching service to customers. In some embodiments, the expert may include a manager of an aesthetic shop or a dermatologist.

In addition, the database 140 may include a user database for storing information about customer who may receive customized services. In this regard, the customer's information may include: basic information about the customer, such as name, affiliation, personal information, gender, age, contact information, e-mail, address, image, etc.; information about the customer's authentication (login), such as ID (or e-mail) and password; information about access country, access location, and a device used for access; and information related to access, such as the connected network environment.

In addition, the user database may store customer-specific information, information and/or category history (for example, diagnosis history, purchase history, etc.) provided by a customer accessing a customized service providing application or a customized service providing site, environment setting information set by the user, resource usage information used by the user, and billing and payment information corresponding to the user's resource usage.

The service providing management unit 150 may transmit survey request information and image request information to the customer terminal 200 in order to diagnose one or more of the customer's skin and scalp. The service providing management unit 150 may collect, from the customer terminal 200, survey response information and images as a response to survey request information and image request information.

The service providing management unit 150 may generate one or more of a skin diagnosis result for the customer's skin and a scalp diagnosis result for the customer's scalp based on the survey response information and image, and provide the same to the customer terminal 200.

The service providing management unit 150 may provide a solution that solves the issue regarding one or more of a skin diagnosis result and a scalp diagnosis result. In particular, the service providing management unit 150 may create and provide recipe information for manufacturing customized products included in the solution, and recommend purchase of customized products corresponding to the recipe information.

The service providing management unit 150 may transmit a manufacturing instruction signal for customized cosmetics including recipe information to the product manufacturing device 300 based on the customized product purchase signal received from the customer terminal 200.

The service providing management unit 150 may transmit maintenance request information to each of the plurality of product manufacturing devices 300 in response to a product purchase request signal from the customer terminal 200. The service providing management unit 150 may receive maintenance response information in response to maintenance request information from each of the plurality of product manufacturing devices 300. The service providing management unit 150 may select at least one of the product manufacturing devices 300 capable of manufacturing a customized product based on the maintenance response information.

The service providing management unit 150 may transmit customized product manufacturing information to the selected product manufacturing device 300 and instruct operation. In the case where a manufacturing completion signal for the customized product is received from the product manufacturing device 300, the service providing management unit 150 may request quality inspection of the customized product. In the case where a quality inspection completion signal for the customized product is received from the product manufacturing device 300, the service providing management unit 150 may request packaging for the customized product. In the case where a packaging completion signal for the customized product is received from the product manufacturing device 300, the service providing management unit 150 may transmit customer shipping information to a shipping company (not shown) and request shipping of the customized product.

The control unit 160, as a kind of central processing unit, may control the operation of the service providing device 100 by driving control software loaded in the program storage unit 130. The control unit 160 may include all types of devices capable of processing data, such as a processor. The term "processor" used herein may refer to a data processing device embedded in hardware, the data processing device having, for example, a physically structured circuit to perform functions expressed by codes or instructions included in a program. Examples of such a data processing device embedded in hardware are a microprocessor, a central processing unit (CPU), a processor core, a multiprocessor, an application-specific integrated circuit (ASIC), and a field programmable gate array (FPGA), and the scope of present disclosure is not limited thereto.

Figure 3:
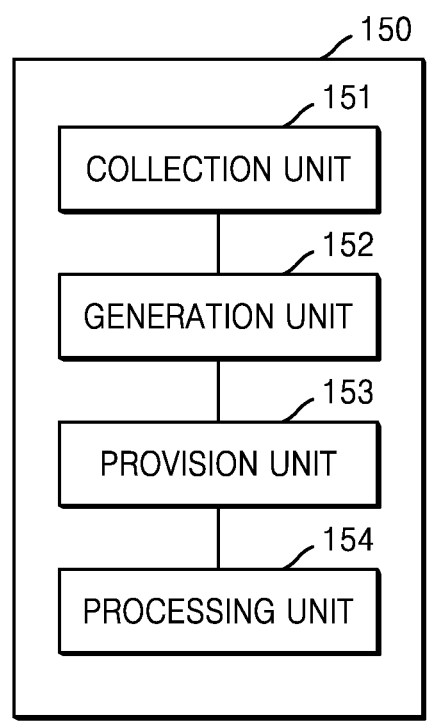
FIG. 3 shows a block diagram schematically illustrating the configuration of a service providing management unit in the customized service providing device of FIG. 2.

FIG. 3 shows a block diagram schematically illustrating the configuration of a service providing management unit in the customized service providing device of FIG. 2, FIG. 4 shows an example diagram of a scalp diagnosis criteria table expressed in MBTI form to generate a customer's scalp diagnosis result according to an embodiment, FIG. 5 shows an example view of a skin diagnosis result for a customer and a solution according to an embodiment, and FIG. 6 shows an example view of a scalp diagnosis result for a customer and a solution according to an embodiment. In the following description, descriptions that have been provided in connection with FIGS. 1 and 2 will be omitted. Referring to FIGS. 3 to 6, the service providing management unit 150 may include a collection unit 151, a generation unit 152, a provision unit 153, and a processing unit 154.

The collection unit 151 may collect survey response information and images from the customer in response to survey request information and image request information provided to the customer to diagnose at least one of a skin of the customer and a scalp of the customer.

The generation unit 152 may generate a diagnosis result for one or more of the customer's skin and scalp based on the survey response information and images.

The generation unit 152 may generate a diagnosis result for skin items including oil and moisture, sensitivity, pigmentation, wrinkles, redness, and pores on the customer's skin as a skin diagnosis result based on survey response information and images.

The generation unit 152 may generate a diagnosis result for pigmentation based on the customer's image. After the generation unit 152 detects a dark pigmented area by using the brightness value of the image, only the melanin pigment may remain when the red pigment is removed using the color difference value. Pigment may be calculated with only the brightness value, and pigmentation may be calculated by giving a primary weight according to the degree of darkness and giving a secondary weight to the degree of darkness compared to the surroundings, adding the two, and dividing the same by the size value of the image.

The generation unit 152 may generate a diagnosis result for wrinkle based on the customer's image. Because wrinkles appear relative to the surroundings like pores, the generation unit 152 detects dark areas in the image, and then, may separately detect and remove hairs which appear similarly dark. Because length and depth are important factors in wrinkles, the generation unit 152 may consider areas with lengths below a certain value and/or depths that are lighter than average to be fine wrinkle lines. The generation unit 152 may calculate the length and depth of the wrinkle by using the S channel of the HLS color for the depth of the wrinkle because the S channel of HLS color has a value similar to the actual depth, and finally multiplying the length by the average depth value in each area determined to be wrinkled, and dividing the same by the size value of the image.

The generation unit 152 may generate a diagnosis result for redness based on the customer's image. Because the R and G color channels of the image are different from those of the surroundings, the generation unit 152 can calculate redness as a combination of the difference between the R color channel and the G color channel and a constant value, and then divide the same by the size value of the image.

The generation unit 152 may generate a diagnosis result for pores based on the customer's image. Because the pore is relatively dark compared to the surroundings thereof and has a round shape, the generation unit 152 detects dark areas in the image, and then, may separately detect and remove hairs which appear similarly dark. The generation unit 152 may use a morphology technique to separate detected pores that are small or elongated and connected. For the value of pores, a size and a depth are important factors. Accordingly, the value of pores may be calculated by multiplying the size by depth for each pixel and dividing the result by the size value of the second image.

In some embodiments, regarding pigmentation, wrinkle, redness, and pore, a diagnosis result may be generated based on the image. However, for oil and moisture and sensitivity, which are difficult to obtain a diagnosis result therefor only with images, diagnosis results for oil and moisture and sensitivity may be generated using images, moisture sensors, oil sensors, survey response results, and analysis algorithms, which are not shown. For example, the customer terminal 200 may include the moisture sensor. In addition, the service providing device 100 may provide the customer with oil paper that can replace the oil sensor.

To generate a diagnosis result for moisture, the generation unit 152 may calculate the amount of moisture on the skin surface by contacting the moisture sensor to the skin surface and measuring the change in capacitance that depends on the distribution of moisture through a precision capacitor. To generate a diagnosis result for oil content, the generation unit 152 may calculate the extent of the oil using a color difference in the red area of an image taken with the oiled paper, because the oil on the oiled paper turns a deeper red color than the original red color of the paper.

To calculate the sensitivity, the generation unit 152 may use a skin analysis algorithm using the customer's survey response information and images for survey request information (for example, does the skin suddenly itch and tingle when the external environment changes, does the pressure mark remain when the forehead is pressed with a fingernail, does changing cosmetics cause tingling or breakouts, etc.). The skin analysis algorithm may use a method of diagnosing moisture and skin reddening, and the results of the skin analysis algorithm and survey response information may be converted into scores.

The generation unit 152 may generate a scalp diagnosis result for scalp items including oil and moisture, sensitivity, hair thickness, hair damage, hair loss, and keratin for the customer's scalp, based on survey response information and images.

The generation unit 152 may use the same method of generating a diagnosis result for oil and moisture and sensitivity of the skin to generate a diagnosis result for oil and moisture and sensitivity of the scalp.

The generation unit 152 may generate a diagnosis result for hair thickness based on the customer's scalp image. After enlarging the customer's scalp image, the generation unit 152 may detect hair using a color difference and calculate the thickness of the detected hair.

The generation unit 152 may generate a diagnosis result for the degree of hair damage based on the survey response information and the customer's scalp image. After enlarging the customer's scalp image, the generation unit 152 may detect hair using color difference, and calculate the degree of hair damage using the roughness and color difference of the detected hair.

The generation unit 152 may generate a diagnosis result for hair loss based on the survey response information and the customer's scalp image. The generation unit 152 may calculate the density of hair by extracting pores from the scalp image, counting the number of hairs visible in the pores, and calculating the number of hairs per unit area. The diagnosis result for hair loss may be calculated using survey response information, the number of hairs per pore, pore density, hair thickness, and forehead width.

The generation unit 152 may generate a diagnosis result for scalp keratin based on the customer's scalp image. The generation unit 152 may calculate the degree of keratinization by detecting light and dark areas in the scalp image relative to the surroundings, excluding the dark areas as hair areas, and converting the light areas to a percentage.

Additionally, the generation unit 152 may use the same method of generating a diagnosis result for skin redness to generate a diagnosis result for scalp redness. The degree of seborrhea (trouble) for the scalp may be calculated using the scalp redness, the scalp degree of keratinization, and the survey response information described above.

As an optional embodiment, the generation unit 152 may use a known keratin measurement algorithm to calculate the degree of keratinization of the scalp. The generation unit 152 may use the survey response information and the oil measurement algorithm to calculate the oil level of the scalp. Generation unit 152 may use survey response information and moisture sensor information to calculate the moisture level of the scalp. The generation unit 152 may use the survey response information, keratin algorithm, and known redness algorithm to calculate the sensitivity of the scalp. The generation unit 152 may use the survey response information, keratin algorithm, and redness algorithm to calculate the degree of seborrhea (trouble) of the scalp. The generation unit 152 may use survey response information, hair number algorithm per pore, pore density algorithm, hair thickness algorithm, and forehead width algorithm to calculate the degree of hair loss. The generation unit 152 may use survey response information and a hair thickness algorithm to calculate the degree of hair damage.

In some embodiments, the generation unit 152 may determine the scalp diagnosis result for the customer as one of a plurality of scalp types classified in the form of MBTI. FIG. 4 shows an example diagram of a scalp diagnosis criteria table expressed in MBTI form to determine a customer's scalp diagnosis result. The scalp diagnosis criteria table is stored in the database 140, and any one type may be selected based on the customer's scalp diagnosis result.

Referring to FIG. 4, a plurality of scalp types classified in the form of MBTI may be classified into 48 scalp types based on 12 scales: dry scalp (D: dry), adequate moisture for neutral scalp and complex scalp (C: complexity), lack of moisture for neutral scalp and complex scalp (P: part), adequate moisture for oily scalp (O: oily), lack of moisture for oily scalp (I: imbalance), resistant scalp (B: barrier), sensitive scalp (S: sensitive), seborrheic scalp (T: trouble), low hair loss concern (N: non), hair loss in progress (A: alopecia), damaged hair (M: damaged), and healthy hair (H: healthy).

If the customer's scalp type is determined to be PSAM shown in FIG. 4, it can be seen that the customer's scalp is neutral/complex, dehydrated and sensitive, and the damaged hair exceeds the threshold, indicating a high risk of hair loss. Additionally, if the customer's scalp type is determined to be OTNM, it can be seen that the customer's scalp is oily and well-moisturized, sensitivity and seborrhea are above the threshold, and damaged hair is above the threshold but at low risk for hair loss.

The provision unit 153 may provide one or more of a skin diagnosis result and a scalp diagnosis result and solution information for addressing issues to the customer terminal 200, and may recommend the purchase of a product that helps in the implementation of the solution.

FIG. 5 shows an example of providing the customer's skin diagnosis result, a solution and product purchase recommendation information to the customer terminal 200.

Figure 5A:
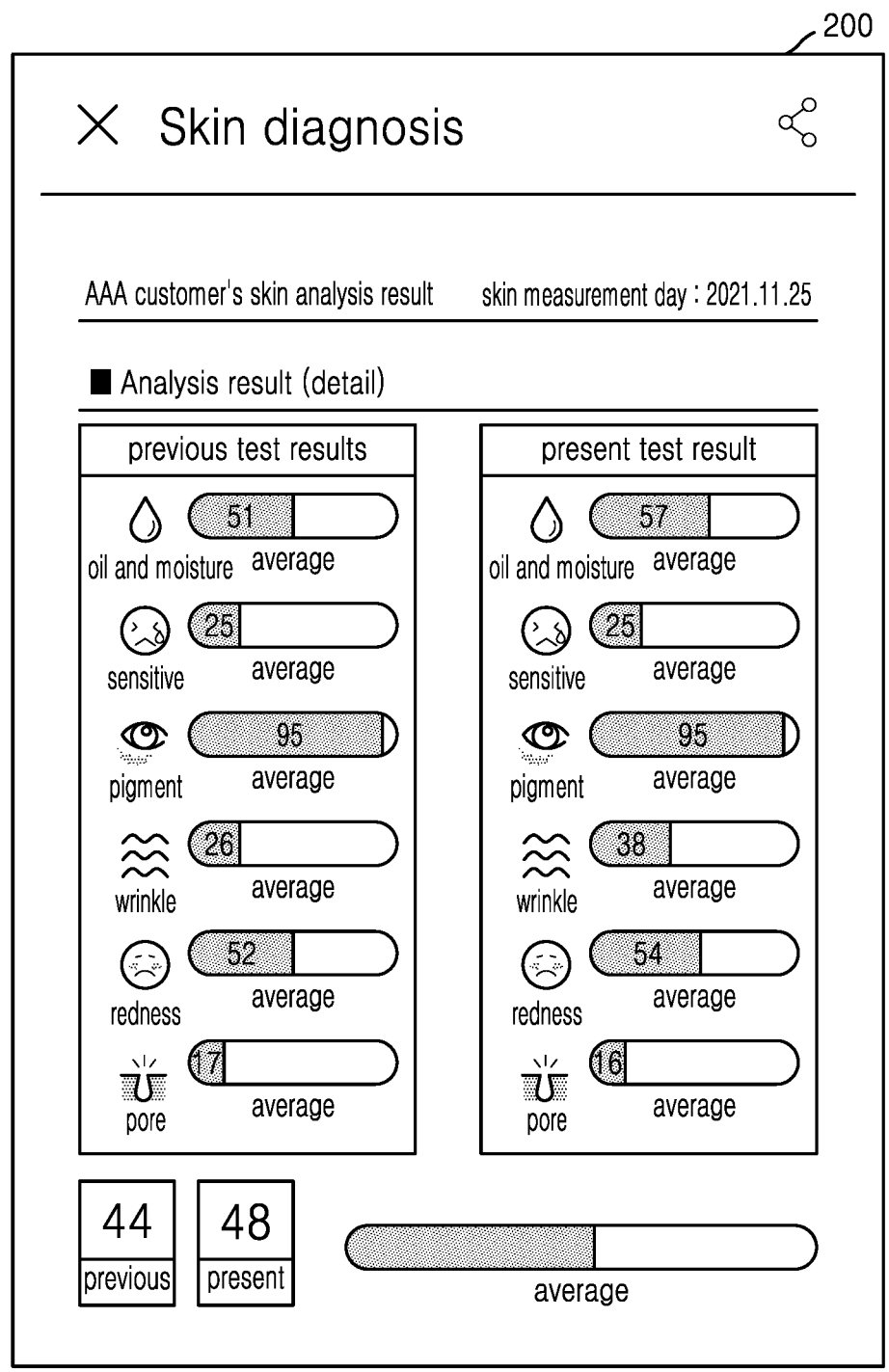

Referring to FIG. 5A, the diagnosis results for skin items including oil and moisture, sensitivity, pigmentation, wrinkles, redness, and pores of the customer's skin are shown, each quantified. In addition, the diagnosis results and averages for all skin items may be quantified and shown. The previous diagnosis result and the current diagnosis result may also be provided together for customers to compare.

Figure 5B:
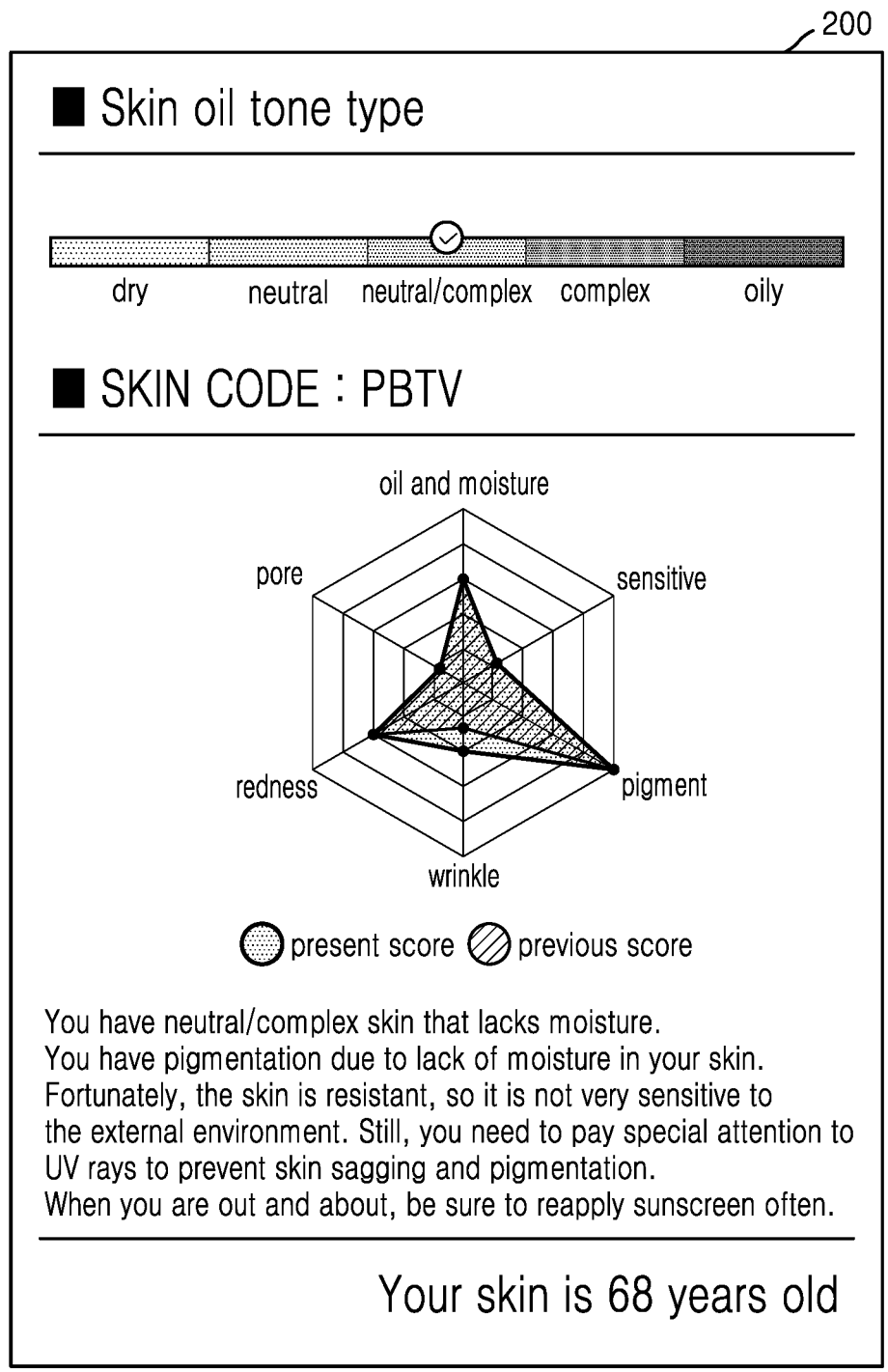

Referring to FIG. 5B, from among oil and tone types of the skin including dry, neutral, neutral/complex, and complex, and oily skin, the oil and tone type of the skin corresponding to a customer may be provided. Skin oil and tone types are provided in the form of a bar, and it is intuitive to see where customers fall in the spectrum. In addition, values of the diagnosis result of the customer's oil and moisture, sensitivity, pigmentation, wrinkles, redness, and pores condition may be tabulated and provided. Previous values and current values are provided together for customers to compare. Comments for addressing issues corresponding to the current skin condition of a customer may be provided, and the customer's skin age according to the skin diagnosis result may be provided.

Figure 5C:
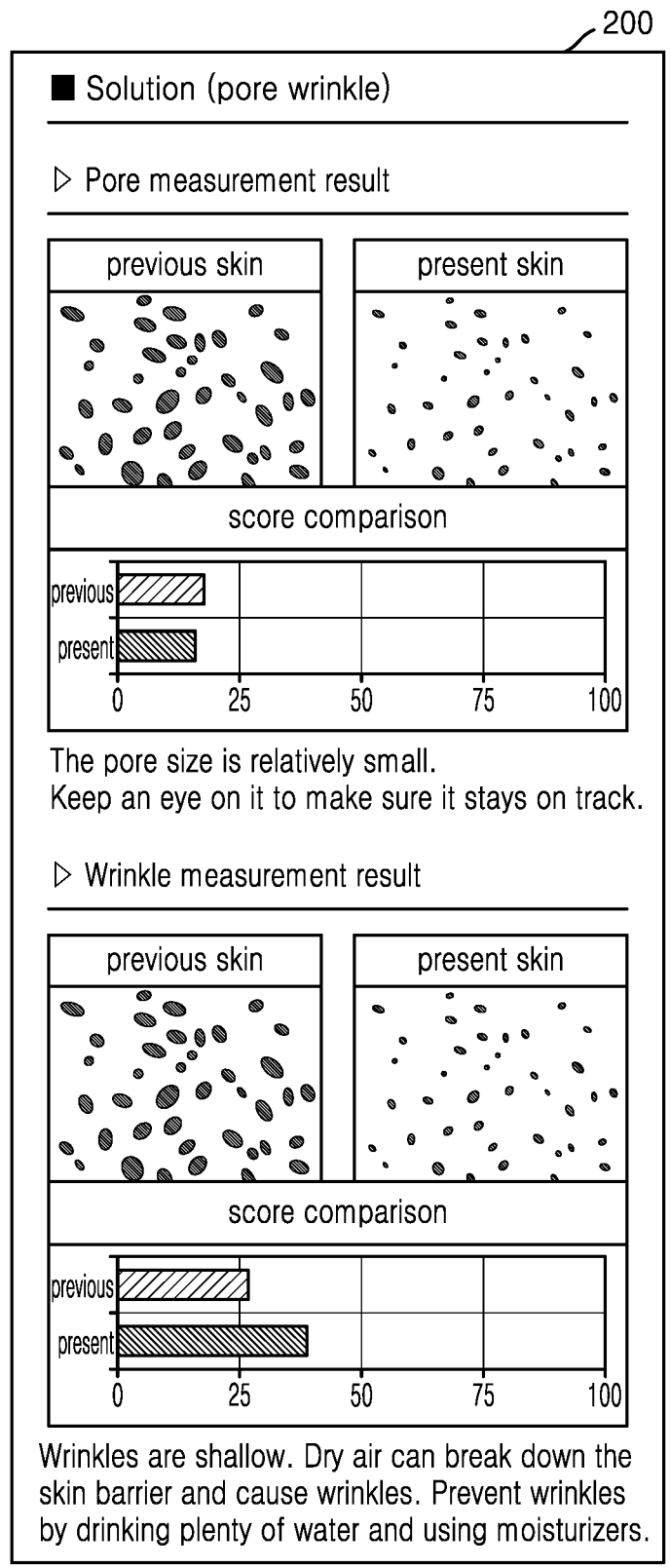

Referring to FIG. 5C, a first solution for skin items may be provided. In some embodiments, skin images and scores for the customer's previous and current pore diagnosis results may be provided, and comments for addressing issues may be provided. In some embodiments, skin images and scores for the customer's previous and current wrinkle diagnosis results may be provided, and comments for addressing issues may be provided.

Referring to FIG. 5D, a second solution for skin items may be provided. For example, a comment for skin care, a skin massage method, and before/after result comparison images provided when skin massage is performed using the corresponding method, may be provided. In addition, the recipe information of the product to provide customized products in response to the customer's skin type corresponding to the skin diagnosis result and the information on the part to be managed intensively may be provided to compare the previous and the present. In addition, comments may be provided on the analysis results for the current diagnosis.

Figure 5E:
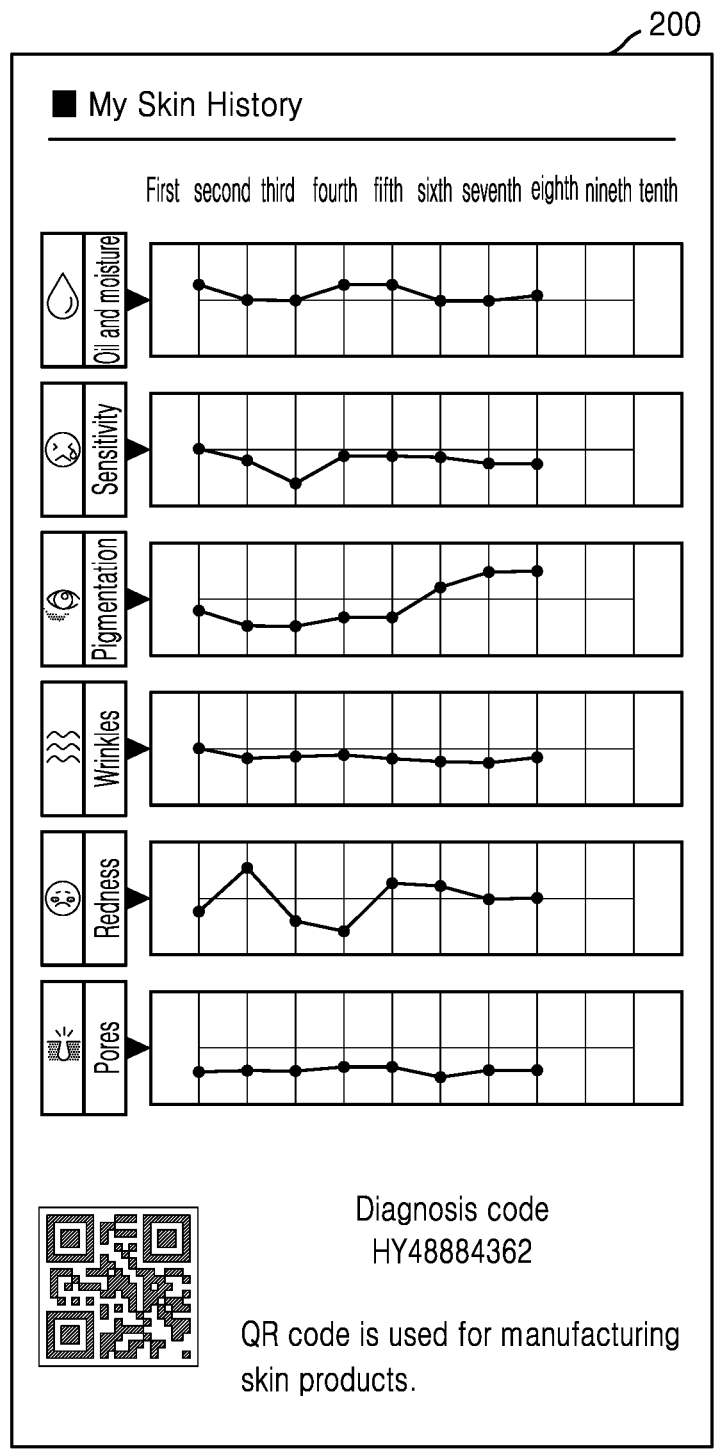

Referring to FIG. 5E, diagnosis history information on skin items including oil and moisture, sensitivity, pigmentation, wrinkles, redness, and pores may be tabulated and provided. For example, a customer may be provided with a graphical representation of the results of the first through seventh skin tests, along with the results of the eighth test performed. With this historical information, customers may intuitively identify changes in their skin. In addition, in response to the customer's skin type described in FIG. 5D, the product recommended to the customer may be provided as a QR code. This QR code may be transmitted to the product manufacturing device 300 in response to a customer's product purchase request.

Figure 5F:

Referring to FIG. 5F, a recommendation program for the customer's skin care, a request menu for receiving contactless coaching service by experts, and a make menu to purchase customized skin products using recipe information corresponding to the diagnosis result, may be provided. When the make menu is selected, a QR code may be sent to the product manufacturing device 300.

FIG. 6 shows an example of providing the customer's scalp diagnosis result, a solution, and product purchase recommendation information to the customer terminal 200.

Figure 6A:
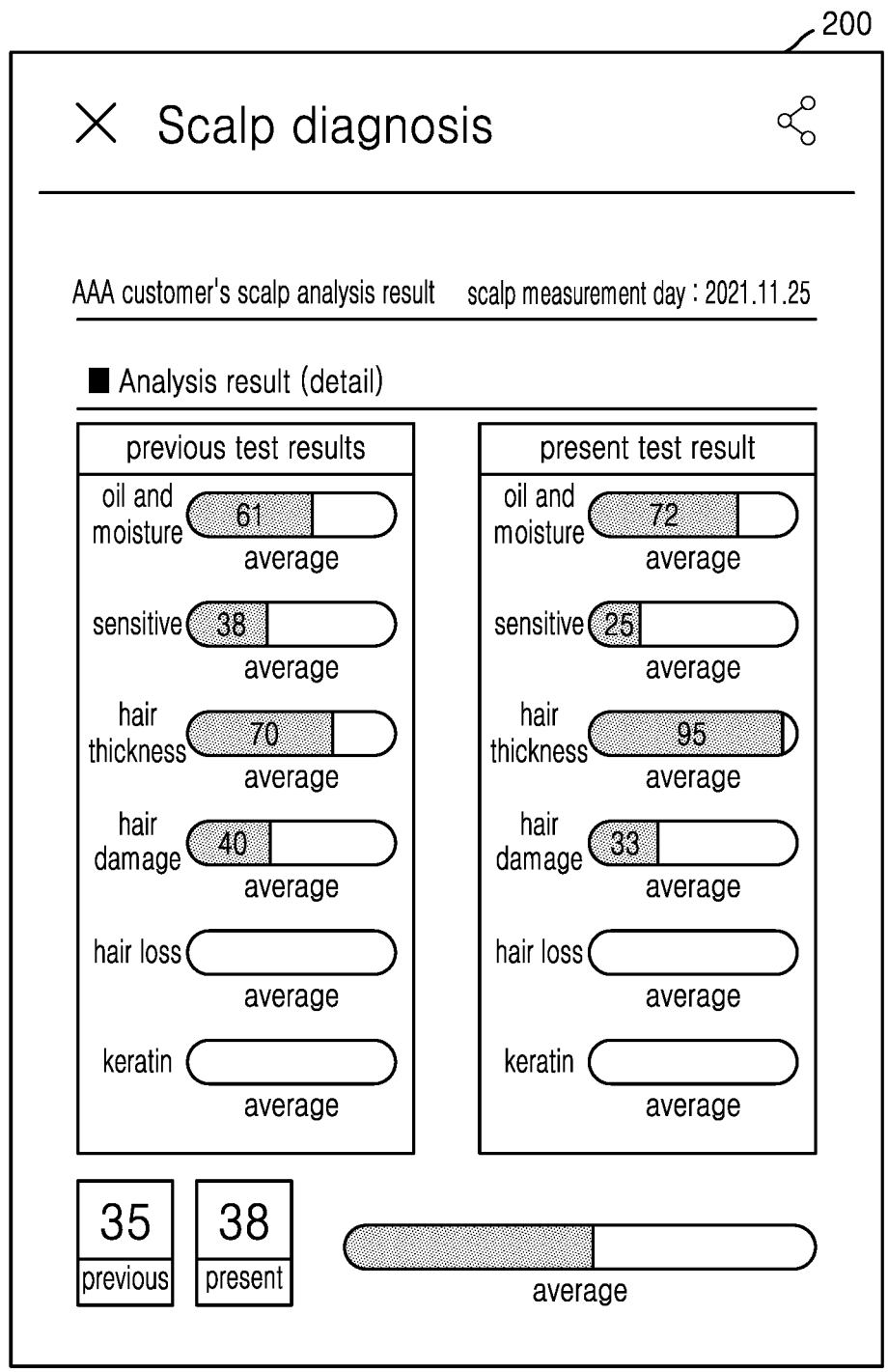

Referring to FIG. 6A, the diagnosis results for scalp items including oil and moisture, sensitivity, hair thickness, hair damage, hair loss, and keratin for the customer's scalp are shown, each quantified. In addition, the diagnosis results and averages for all scalp items may be quantified and shown. The previous diagnosis result and the current diagnosis result may also be provided together for customers to compare.

Figure 6B:
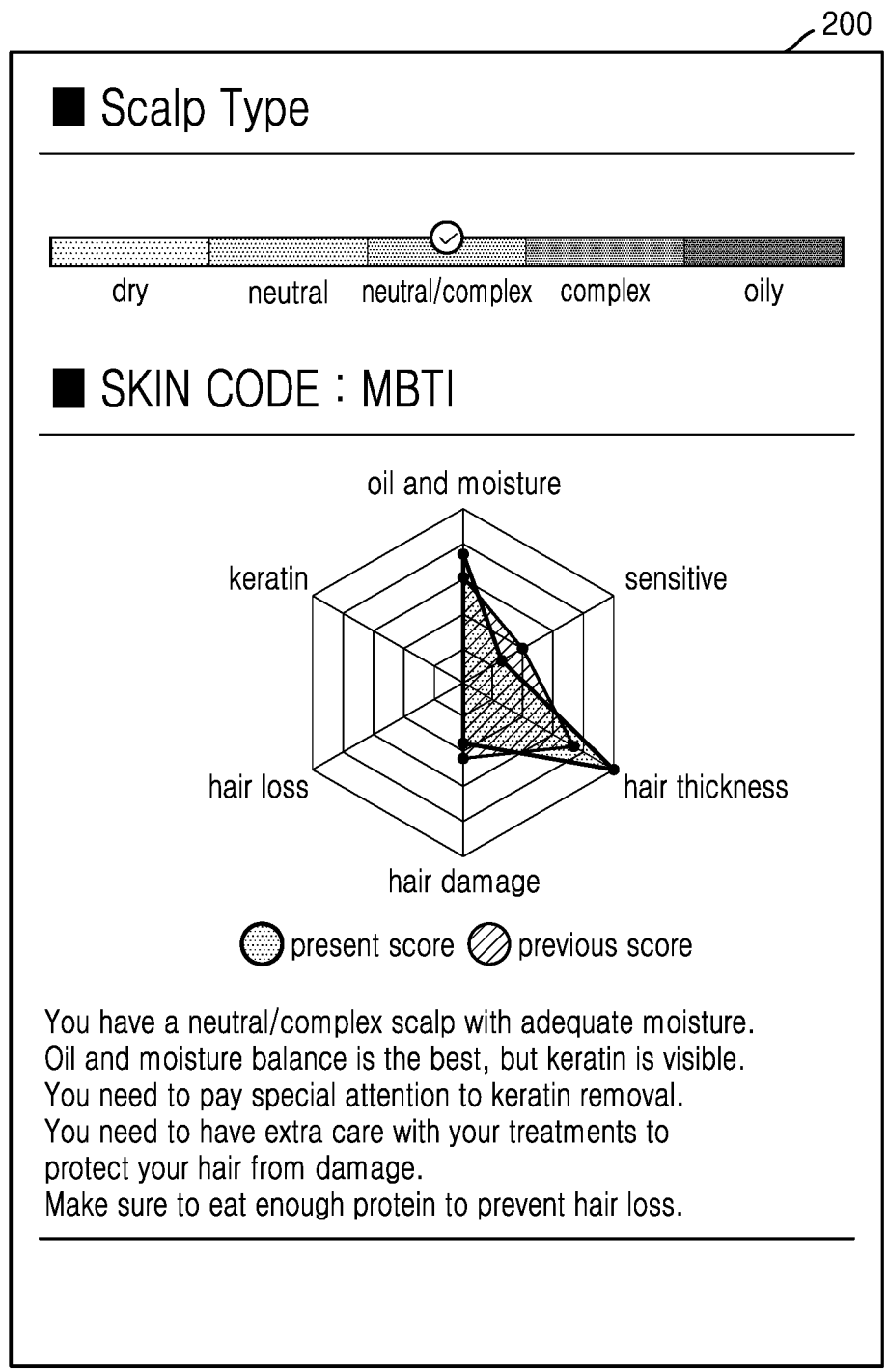

Referring to FIG. 6B, from among oil and tone types of the skin including dry, neutral, neutral/complex, and complex, and oily skin, the oil and tone type of the scalp corresponding to a customer may be provided. Scalp oil and tone types are provided in the form of a bar, and it is intuitive to see where customers fall in the spectrum. In addition, the diagnosis result for the customer's scalp may be determined and provided as one of a plurality of scalp types classified in the form of MBTI. In addition, values of the diagnosis result of the customer's oil and moisture, sensitivity, hair thickness, hair damage, hair loss, and keratin may be tabulated and provided. Previous values and current values are provided together for customers to compare. In addition, comments for addressing issues in response to the customer's current scalp condition, may be provided.

Figure 6C:
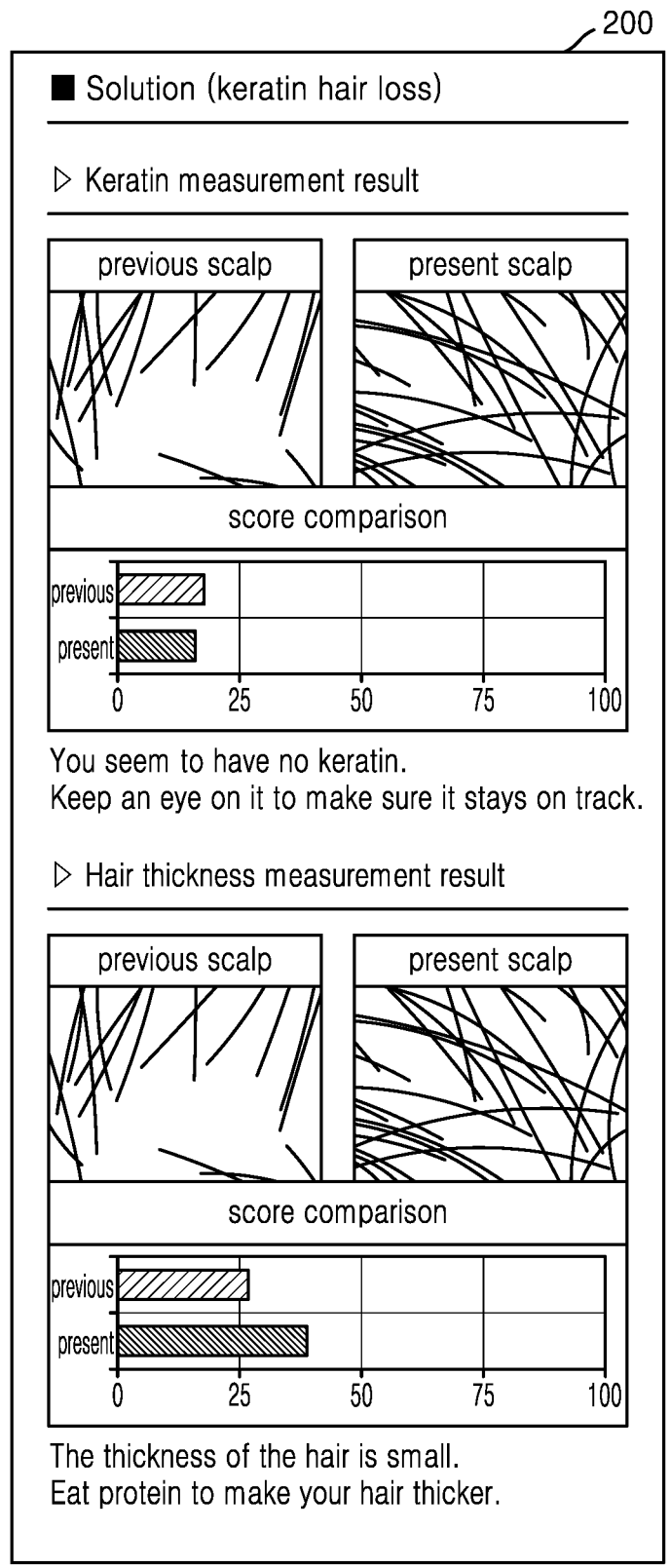

Referring to FIG. 6C, a first solution for scalp items may be provided. In some embodiments, scalp images and scores for the customer's previous and current keratin diagnosis results may be provided, and comments for addressing issues may be provided. In some embodiments, scalp images and scores for the customer's previous and current hair loss diagnosis results may be provided, and comments for addressing issues may be provided.

Referring to FIG. 6D, a second solution for scalp items may be provided. As an example, comments for scalp management and scalp massage methods may be provided. In addition, the recipe information of the product to provide customized products in response to the customer's scalp type corresponding to the scalp diagnosis result and the information on the part to be managed intensively may be provided to compare the previous and the present. In addition, comments may be provided on the analysis results for the current diagnosis.

Figure 6E:
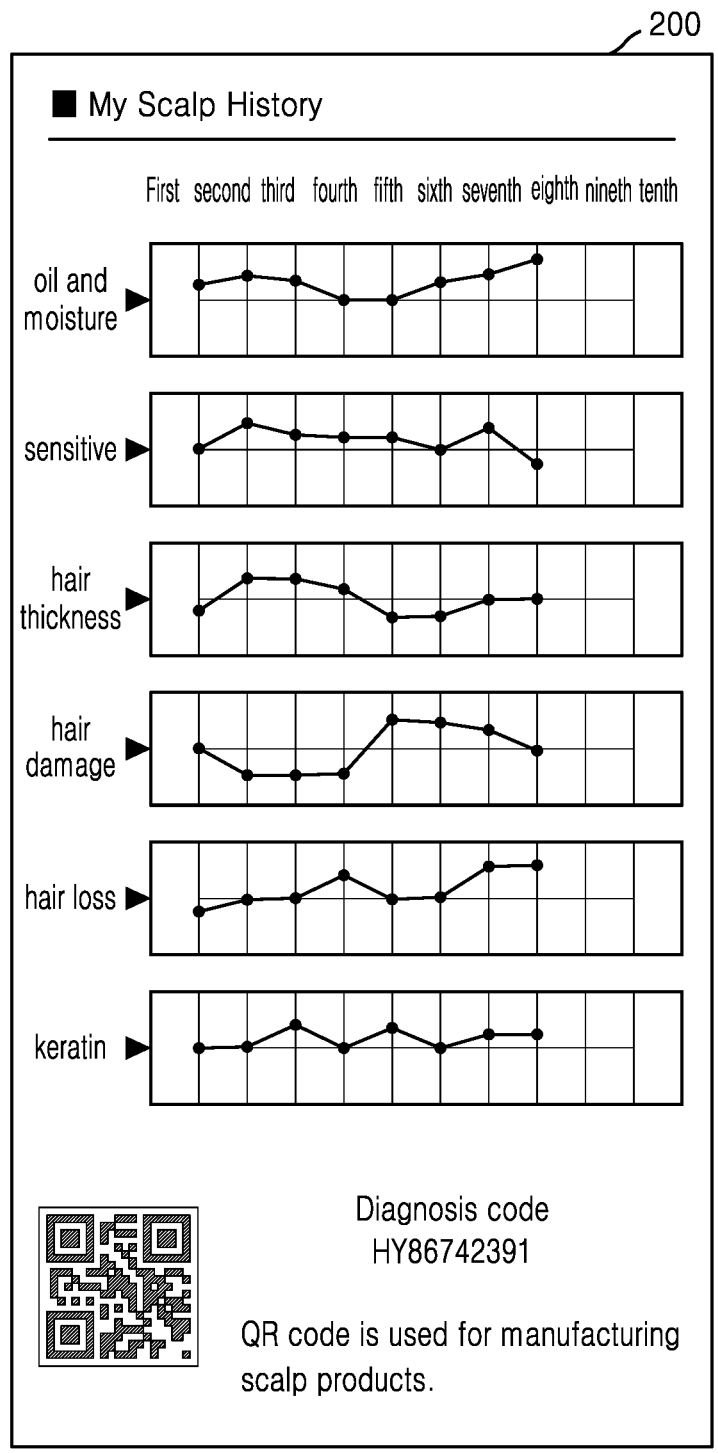

Referring to FIG. 6E, diagnostic history information on scalp items including oil and moisture, sensitivity, hair thickness, hair damage, hair loss, and keratin may be tabulated and provided. For example, a customer may be provided with a graphical representation of the results of the first through seventh scalp tests, along with the results of the eighth test performed. With this historical information, customers may intuitively identify changes in their scalp. In addition, in response to the customer's scalp type described in FIG. 6D, the product recommended to the customer may be provided as a QR code. This QR code may be transmitted to the product manufacturing device 300 in response to a customer's product purchase request.

Figure 6F:

Referring to FIG. 6F, a recommendation program for the customer's scalp care, a request menu for receiving contactless coaching service by experts, and a make menu to purchase customized scalp products using recipe information corresponding to the diagnosis result, may be provided. When the make menu is selected, a QR code may be sent to the product manufacturing device 300.

In some embodiments, the provision unit 153 may provide recipe information to purchase a customized skin product and a scalp product. For example, provided is at least one of the following products: an oily light type product that is a light formulation and is quickly absorbed into the skin, a universal media type product suitable for both oily and dry types, a dry heavy type product that covers the skin surface for a long time, a heavy type product that covers the epidermis surface of the skin for a long time, a light type product that is a light formulation and is quickly absorbed into the skin, a lifting product that is an anti-wrinkle patented herbal complex and improves skin wrinkles, a brightening product that includes a plant raw material having whitening ingredients and inhibits melanin synthesis, a moisturizing product that retains high moisturizing and moisture retention using hyaluronic acid, which is a moisturizing ingredient, an elasticity product for creating skin elasticity and strengthening elasticity using human collagen, a trouble-solving product that can improve skin condition using antibacterial and anti-acne patented ingredients, a soothing product that moisturizes the skin and provides a soothing effect with six herbs, a sebum control product that adjusts the amount of sebum by matching the oil and moisture balance of the skin, and a pore product that prevents pore expansion by stabilizing the generation cycle of the keratin layer, may be provided. In some embodiments, the raw material of the product included in the recipe information may be changed rather than fixed, and may be optimized while changing the raw material of the product.

In some embodiments, the provision unit 153 may provide a contactless coaching service to the customer terminal 200 to address issues regarding one or more of a skin diagnosis result and a scalp diagnosis result. The provision unit 153 may provide the contactless coaching service when a selection of the contactless coaching service request menu shown in FIGS. 5F and 6F is received from the customer terminal 200. The provision unit 153 may match customer-specific experts to provide contactless coaching services. In some embodiments, profile information of various experts may be stored in the database 140. The provision unit 153 may select an expert corresponding to one or more of the customer's diagnosis result and the scalp diagnosis result and match the expert with the customer. In some embodiments, a customer may directly view profile information of experts and select an expert to receive a coaching service.

The provision unit 153 may obtain coaching data based on one or more of a skin diagnosis result and a scalp diagnosis result generated by an expert from the matched expert terminal, product recipe information for one or more of a skin diagnosis result and a scalp diagnosis result, manufactured customized cosmetics, skin history information, and skin care information, and provide the same to the customer terminal 200. In this process, 1:1 contactless counseling may be performed between the customer and the expert. The provision unit 153 may provide the coaching data generated by the expert to the customer terminal 200 at preset times and/or intervals.

The processing unit 154 may transmit maintenance request information to each of the plurality of product manufacturing devices 300 in response to a product purchase request signal from a customer. In some embodiments, when the manufacturing menu of FIGS. 5E and 6E is selected, a product purchase request signal from the customer may be received by the processing unit 154. In addition, the maintenance request information may include raw material inventory request information, container inventory request information, status request information, and manufacturing environment request information, of each of the product manufacturing devices 300.

The processing unit 154 may receive maintenance response information in response to maintenance request information from each of the plurality of product manufacturing devices 300. In some embodiments, the maintenance response information may include raw material inventory response information, container inventory response information, status response information, and manufacturing environment response information. In some embodiments, the status response information may include whether or not the product manufacturing device 300 is operating normally, the number of production instructions, the number of manufacturing completions, the defect rate, workers, the manufacturing progress phase (for example, container insertion, container separation, raw material discharge, container coupling, stirring, etc.), raw material discharge amount, raw material expiration date, raw material order status, raw material purchase status, etc. In addition, the manufacturing environment response information may include temperature and humidity inside the product manufacturing device 300 and internal cleanliness thereof.

The processing unit 154 may select at least one of the product manufacturing devices 300 capable of manufacturing a customized product based on the maintenance response information received from each of the plurality of product manufacturing devices 300, transmit the customized product manufacturing information to the product manufacturing device 300 and instruct an operation. In this regard, the customized product manufacturing information may include one or more of recipe information corresponding to one or more of a skin diagnosis result and a scalp diagnosis result for the customer, raw material formulation information, container information, and mixing information.

In the case where a manufacturing completion signal for the customized product is received from the product manufacturing device 300, the processing unit 154 may request quality inspection of the customized product. In some embodiments, the quality inspection of the customized product may be performed in the product manufacturing device 300. Alternatively, the product manufacturing device 300 which has received the request of the processing unit 154, may commission an external quality evaluation company (not shown) to perform a quality inspection.

In the case where a quality inspection completion signal for the customized product is received from the product manufacturing device 300, the processing unit 154 may request packaging for the customized product.

In the case where a packaging completion signal for the customized product is received from the product manufacturing device 300, the processing unit 154 may transmit customer shipping information to a shipping company (not shown) and request shipping of the customized product. The shipping company may pick up the customized product from the warehouse of the product manufacturing device 300 and ship the same to the customer.

Figure 7:
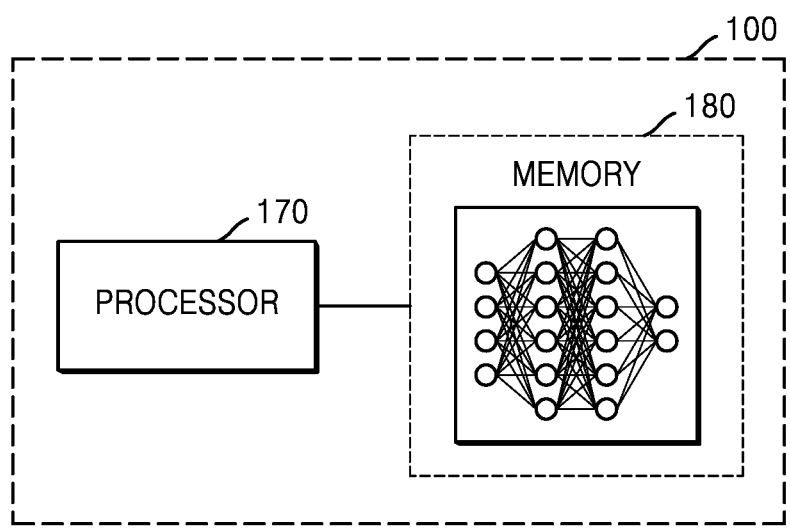
FIG. 7 shows a block diagram schematically illustrating the configuration of a customized service providing device according to an embodiment.

FIG. 7 shows a block diagram schematically illustrating the configuration of a customized service providing device according to an embodiment; and In the following description, descriptions that have been provided in connection with FIGS. 1 to 6 will be omitted. Referring to FIG. 7, a service providing device 100 according to another embodiment may include a processor 170 and a memory 180.

In some embodiments, the processor 170 may process functions performed by the communication unit 110, the storage media 120, the program storage unit 130, the database 140, the service providing management unit 150, and the control unit 160, which are shown in FIGS. 2 and 3.

This processor 170 may control the entire operation of the service providing device 100. The term "processor" used herein may refer to a data processing device embedded in hardware, the data processing device having, for example, a physically structured circuit to perform functions expressed by codes or instructions included in a program. Examples of such a data processing device embedded in hardware are microprocessors, central processing units, processor cores, multiprocessors, ASICs, and FPGAs, but the scope of present disclosure is not limited thereto.

The memory 180 may be operatively connected to the processor 170 and may store at least one code associated with an operation performed by the processor 170.

In addition, the memory 180 may temporarily or permanently store data processed by the processor 170, and may include data built into the database 140. In this regard, memory 180 may include magnetic storage media or flash storage media, but the scope of present disclosure is not limited thereto. The memory 180 may include built-in memory and/or external memory, and may include: a volatile memory such as DRAM, SRAM, or SDRAM, a non-volatile memory such as one time programmable ROM (OTPROM), PROM, EPROM, EEPROM, mask ROM, flash ROM, NAND flash memory, or NOR flash memory, a flash drive such as SSD, a compact flash (CF) card, an SD card, a micro-SD card, a mini-SD card, an Xd card, or a memory stick, or a storage device such as an HDD.

FIG. 8 shows a flowchart for explaining a method of providing a customized service according to an embodiment. In the following description, descriptions that have been provided in connection with FIGS. 1 to 7 will be omitted. According to an embodiment, the customized service providing method will be described assuming that the service providing device 100 is performed by the processor 170 with the help of peripheral components.

Referring to FIG. 8, in operation S810, the processor 170 may transmit survey request information and image request information to the customer terminal 200 connected through the network 400 to diagnose one or more of the skin of the customer and the scalp of the customer, and may collect survey response information and images as a response to the survey request information and image request information from the customer terminal 200.

In operation S820, the processor 170 may generate one or more of a skin diagnosis result for the customer's skin and a scalp diagnosis result for the customer's scalp based on the survey response information and images, and provide the same to the customer terminal 200. The processor 170 may generate, as a skin diagnosis result, a diagnosis result for skin items including oil and moisture, sensitivity, pigmentation, wrinkles, redness, and pores on the customer's skin. In addition, the processor 170 may generate, as a scalp diagnosis result, a diagnosis result for scalp items of the customer's scalp including oil and moisture, sensitivity, hair thickness, hair damage, hair loss, and keratin. In some embodiments, the processor 170 may determine the scalp diagnosis result as one of a plurality of scalp types classified in MBTI form. In this regard, a plurality of scalp types classified in the form of MBTI may be classified into 48 scalp types based on 12 scales: dry scalp (D: dry), adequate moisture for neutral scalp and complex scalp (C: complexity), lack of moisture for neutral scalp and complex scalp (P: part), adequate moisture for oily scalp (O: oily), lack of moisture for oily scalp (I: imbalance), resistant scalp (B: barrier), sensitive scalp (S: sensitive), seborrheic scalp (T: trouble), low hair loss concern (N: non), hair loss in progress (A: alopecia), damaged hair (M: damaged), and healthy hair (H: healthy).

In operation S830, the processor 170 may generate recipe information for manufacturing a customized product in response to one or more of a skin diagnosis result and a scalp diagnosis result and provide the same to the customer terminal 200. In some embodiments, the processor 170 may recommend purchase of a customized product corresponding to the recipe information.

In operation S840, in the case where the customized product purchase signal is received, the processor 170 may transmit customized product manufacturing information including recipe information and a manufacturing instruction signal for customized cosmetics to the product manufacturing device 300.

FIG. 9 shows a flowchart for explaining a method of providing a customized service according to an embodiment. In the following description, descriptions that have been provided in connection with FIGS. 1 to 8 will be omitted. According to an embodiment, the customized service providing method will be described assuming that the service providing device 100 is performed by the processor 170 with the help of peripheral components.

Referring to FIG. 9, in operation S810, the processor 170 may transmit survey request information and image request information to the customer terminal 200 connected through the network 400 to diagnose one or more of the customer's skin and scalp, and may collect survey response information and images as a response to the survey request information and image request information from the customer terminal 200.

In operation S920, the processor 170 may generate one or more of a skin diagnosis result for the customer's skin and a scalp diagnosis result for the customer's scalp based on the survey response information and images, and provide the same to the customer terminal 200.

In operation S930, the processor 170 may generate recipe information for manufacturing a customized product in response to one or more of a skin diagnosis result and a scalp diagnosis result and provide the same to the customer terminal 200. In some embodiments, the processor 170 may recommend purchase of a customized product corresponding to the recipe information.

In operation S940, the processor 170 may determine whether a product purchase request signal is received from the customer terminal 200.

In operation S950, in the case where the product purchase request signal is received from the customer terminal 200, the processor 170 may transmit customized product manufacturing information including recipe information to the product manufacturing device 300, and instruct an operation. In some embodiments, the processor 170 may transmit maintenance request information to each of the plurality of product manufacturing devices 300 before instructing the product manufacturing device 300 to perform an operation. The processor 170 may receive maintenance response information in response to maintenance request information from each of the plurality of product manufacturing devices 300. The processor 170 may select at least one of the product manufacturing devices 300 capable of manufacturing a customized product based on the maintenance response information.

In the case where a manufacturing completion signal for the customized product is received from the product manufacturing device 300, the processor 170 may request quality inspection of the customized product.

In operation S970, in the case where a quality inspection completion signal for the customized product is received from the product manufacturing device 300, the processor 170 may request packaging for the customized product.

In operation S980, in the case where a packaging completion signal for the customized product is received from the product manufacturing device 300, the processor 170 may transmit customer shipping information to a shipping company (not shown) and request shipping of the customized product.

Embodiments according to the present disclosure described hereinbefore may be implemented in the form of a computer program that can be executed on a computer through various components, and such a computer program may be recorded on a computer-readable media. In this regard, the media may include magnetic media such as hard disks, floppy disks and magnetic tapes, optical recording media such as CD-ROM and DVD, magneto-optical media such as floptical disks, hardware devices specially configured to store and execute program instructions, such as ROM, RAM, and flash memory.

Meanwhile, the computer program may be specially designed and configured for present disclosure, or may be known and available to those skilled in the art of computer software. Examples of computer programs may include not only machine language codes generated by a compiler but also high-level language codes that can be executed by a computer using an interpreter or the like.

In the specification of the present disclosure (particularly in the claims), the use of the term "the" and indicating terms similar thereto may correspond to both singular and plural. In addition, when a range is described in the present disclosure, it includes the disclosure to which individual values belonging to the range are applied (unless there is no description to the contrary), as if each individual value constituting the range were recited in the detailed description of the disclosure.

If there is no clear or contrary description of the order of the steps constituting the method according to the present disclosure, the operations may be performed in a suitable order. The present disclosure is not necessarily limited according to the order of description of the operations. The use of all examples or exemplary terms (for example, etc.) in the present disclosure is simply for explaining the present disclosure in detail, and the scope of the present disclosure is not limited by the examples or exemplary terms unless they are limited by the claims. In addition, those skilled in the art can appreciate that various modifications, combinations and changes can be made according to design conditions and factors within the scope of the appended claims or equivalents thereof.

Therefore, the concept of the present disclosure should not be limited to the embodiments, and not only the claims to be described later, but also all ranges equivalent to or equivalently changed from the claims would fall within the scope of the concept of the present disclosure.

The present disclosure can help a customer manage his or her skin by generating a diagnosis result for a customer's skin from a customer's image and survey response results, and manufacturing and providing a customized skin product based on the recipe information generated according to the diagnosis result.

The present disclosure can also help a customer manage his or her scalp by generating a diagnosis result for a customer's scalp from a customer's image and survey response results, and manufacturing and providing a customized scalp product based on the recipe information generated according to the diagnosis result.

In addition, by determining and providing the diagnosis result for the customer's scalp as one of a plurality of scalp types classified in the form of MBTI, the customer's own scalp condition can be intuitively recognized and corresponding management methods can be easily learned.

In addition, customer's skin and/or scalp management satisfaction can be improved by the manufacture of a customized skin product and/or scalp product by the product manufacturing device based on the recipe information generated according to the diagnosis result in the case where a purchase request for skin product and/or scalp product is received from the customer.

Although skin products and/or scalp products are a mass-produced, uniform product, the customer recognizes the skin products and/or scalp products as a personalized product, so customer satisfaction with the products can be improved.

The effects of the present disclosure are not limited to those described above, and other effects not described will be apparent to those skilled in the art from the following description.

Although certain embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A method for providing customized service, the method comprising the steps of:
providing at least one customized service providing device;
providing at least one product manufacturing device;
collecting survey response information and images from a customer in response to survey request information and image request information provided to a customer to diagnose at least one of a skin of the customer and a scalp of the customer;
generating a diagnosis result for the at least one of a skin of the customer and a scalp of the customer based on the survey response information and images, wherein the step of generating the diagnosis result includes a step of generating, based on the survey response information and the images, a scalp diagnosis result for scalp items for the customer's scalp including hair thickness, hair damage, hair loss, and keratin;
generating and providing recipe information for manufacturing a customized product corresponding to the diagnosis result;
transmitting maintenance request information including raw material inventory request information, container inventory request information, status request information, and manufacturing environment request information to the at least one product manufacturing device;
receiving, from the at least one product manufacturing device, maintenance response information including raw material inventory response information, container inventory response information, status response information, and manufacturing environment response information, in response to the maintenance request information;
transmitting a manufacturing instruction signal of a customized product including the recipe information to the at least one product manufacturing device based on a customized product purchase signal received from the customer;
manufacturing the customized product with the at least one product manufacturing device based on the maintenance response information; and
sending a manufacturing completion signal for the customized product with the at least one product manufacturing device,
wherein the survey request information includes questions corresponding to at least one of a frequency with which the customer washes his or her face, a degree of skin tightness before and after the face is washed, types of skin products currently being used by the customer, a number of times the customer washes his or her hair, a degree of scalp tightness after the customer washes his or her hair, and types of hair products being used by the customer, wherein the scalp diagnosis result for scalp items for the customer's scalp further includes oil and moisture, and sensitivity, wherein the step of generating the diagnosis result further includes determining the scalp diagnosis result for the customer as one of a plurality of scalp type indicators, and classifying each of the plurality of scalp type indicators as a corresponding personality type indicator, and wherein the plurality of scalp type indicators include:
48 scalp type indicators based on 12 scales: dry scalp (D: dry), adequate moisture for neutral scalp and complex scalp (C: complexity), lack of moisture for neutral scalp and complex scalp (P: part), adequate moisture for oily scalp (O: oily), lack of mois ture for oily scalp (1: imbalance), resistant scalp (B: barrier), sensitive scalp (S: sensitive), seborrheic scalp (T: trouble), low hair loss concern (N: non), hair loss in progress (A: alopecia), damaged hair (M: damaged), and health hair (H: healthy).

2. A method for providing customized service, the method comprising the steps of:
providing at least one customized service providing device;
providing at least one product manufacturing device;
collecting survey response information and images from a customer in response to survey request information and image request information provided to a customer to diagnose at least one of a skin of the customer and a scalp of the customer;
generating a diagnosis result for the at least one of a skin of the customer and a scalp of the customer based on the survey response information and images, wherein the step of generating the diagnosis result includes a step of generating, based on the survey response information and the images, a scalp diagnosis result for scalp items for the customer's scalp including hair thickness, hair damage, hair loss, and keratin;
generating and providing recipe information for manufacturing a customized product corresponding to the diagnosis result;
transmitting maintenance request information including raw material inventory request information, container inventory request information, status request information, and manufacturing environment request information to the at least one product manufacturing device;
receiving, from the at least one product manufacturing device, maintenance response information including raw material inventory response information, container inventory response information, status response information, and manufacturing environment response information, in response to the maintenance request information;
transmitting a manufacturing instruction signal of a customized product including the recipe information to the at least one product manufacturing device based on a customized product purchase signal received from the customer;
manufacturing the customized product with the at least one product manufacturing device based on the maintenance response information; and
sending a manufacturing completion signal for the customized product with the at least one product manufacturing device,
wherein the survey request information includes questions corresponding to at least one of a frequency with which the customer washes his or her face, a degree of skin tightness before and after the face is washed, types of skin products currently being used by the customer, a number of times the customer washes his or her hair, a degree of scalp tightness after the customer washes his or her hair, and types of hair products being used by the customer, and wherein the survey request information includes questions corresponding to each of the frequency with which the customer washes his or her face, the degree of skin tightness before and after the face is washed, the types of skin products currently being used by the customer, a number of times the customer washes his or her hair, the degree of scalp tightness after the customer washes his or her hair, and the types of hair products being used by the customer.

3. A method for providing customized service, the method comprising the steps of:
providing at least one customized service providing device;
providing at least one product manufacturing device;
collecting survey response information and images from a customer in response to survey request information and image request information provided to a customer to diagnose at least one of a skin of the customer and a scalp of the customer;
generating a diagnosis result for the at least one of a skin of the customer and a scalp of the customer based on the survey response information and images, wherein the step of generating the diagnosis result includes a step of generating, based on the survey response information and the images, a scalp diagnosis result for scalp items for the customer's scalp including hair thickness, hair damage, hair loss, and keratin;
generating and providing recipe information for manufacturing a customized product corresponding to the diagnosis result;
transmitting maintenance request information including raw material inventory request information, container inventory request information, status request information, and manufacturing environment request information to the at least one product manufacturing device;
receiving, from the at least one product manufacturing device, maintenance response information including raw material inventory response information, container inventory response information, status response information, and manufacturing environment response information, in response to the maintenance request information;
transmitting a manufacturing instruction signal of a customized product including the recipe information to the at least one product manufacturing device based on a customized product purchase signal received from the customer;
manufacturing the customized product with the at least one product manufacturing device based on the maintenance response information; and
sending a manufacturing completion signal for the customized product with the at least one product manufacturing device,
wherein the survey request information includes questions corresponding to at least one of a frequency with which the customer washes his or her face, a degree of skin tightness before and after the face is washed, types of skin products currently being used by the customer, a number of times the customer washes his or her hair, a degree of scalp tightness after the customer washes his or her hair, and types of hair products being used by the customer, and wherein the method for comprises commissioning an external quality evaluation company with the product manufacturing device to perform a quality inspection of the customized product.

4. The method of claim 3, wherein the
scalp diagnosis result for scalp items for the customer's scalp further includes oil and moisture, and sensitivity.

5. The method of claim 4, wherein the step of generating the diagnosis result further includes determining the scalp diagnosis result for the customer as one of a plurality of scalp type indicators, and classifying each of the plurality of scalp type indicators as a corresponding personality type indicator.

6. The method of claim 3, further comprising a step of providing a contactless coaching service to the customer after the step of generating the diagnosis result,
wherein the step of providing the contactless coaching service includes the steps of:
matching experts for each customer;
obtaining a diagnosis result for the at least one of a skin of the customer and a scalp of the customer generated by a matched expert and coaching data based on recipe information corresponding to the diagnosis result for the at least one of a skin of the customer and a scalp of the customer and manufactured customized product information; and
providing the coaching data to the customer at a preset time and/or a preset period.

7. The method of claim 3, further comprising the steps of:
after the step of transmitting the manufacturing instruction signal of the customized products to the product manufacturing device:
requesting quality inspection of the customized product in the case where a manufacturing completion signal for the customized product is received from the product manufacturing device;
requesting packaging of the customized product in the case where a quality inspection completion signal for the customized product is received from the product manufacturing device; and
transmitting customer shipping information to a shipping company in the case where a packaging completion signal for the customized product is received from the product manufacturing device and requesting shipping of the customized product.

8. The method of claim 3, wherein causing the at least one product manufacturing device to manufacture the customized product comprises mixing different materials with the at least one product manufacturing device to manufacture the customized product.

9. The method of claim 3, further comprising receiving from the product manufacturing device a packaging completion signal for the customized product, and in response, transmitting from the service providing device customer shipping information to a shipping company and requesting shipping of the customized product.

10. The method of claim 9, wherein the survey request information includes questions corresponding to each of the frequency with which the customer washes his or her face, the degree of skin tightness before and after the face is washed, the types of skin products currently being used by the customer, a number of times the customer washes his or her hair, the degree of scalp tightness after the customer washes his or her hair, and the types of hair products being used by the customer.

11. The method of claim 3, further comprising performing packaging for the customized product with the at least one product manufacturing device in response to a packaging request signal for a customized product.

12. The method of claim 3, further comprising transmitting a quality inspection result of the customized product to the customized service providing device with the at least one product manufacturing device.

13. The method of claim 3, further comprising sending maintenance response information in response to maintenance request information from the at least one product manufacturing device.

* * * * *